(12) United States Patent
Barker et al.

(10) Patent No.: US 11,440,867 B2
(45) Date of Patent: Sep. 13, 2022

(54) MEDICAL LUBRICANT

(71) Applicant: KVI LLC, Eden Prairie, MN (US)

(72) Inventors: Alan Thomas Barker, Bloomington, IN (US); Thomas P. Clement, Bloomington, IN (US)

(73) Assignee: KVI LLC, Eden Prairie, MN (US)

( * ) Notice: Subject to any disclaimer, the term of this patent is extended or adjusted under 35 U.S.C. 154(b) by 0 days.

(21) Appl. No.: 16/389,694

(22) Filed: Apr. 19, 2019

(65) Prior Publication Data
US 2019/0337878 A1 Nov. 7, 2019

Related U.S. Application Data

(60) Provisional application No. 62/667,778, filed on May 7, 2018.

(51) Int. Cl.
| | |
|---|---|
| *C10M 169/00* | (2006.01) |
| *C07C 55/22* | (2006.01) |
| *C07C 53/00* | (2006.01) |
| *C07C 55/02* | (2006.01) |
| *C07F 9/06* | (2006.01) |
| *C10M 105/32* | (2006.01) |
| *C10M 137/04* | (2006.01) |

(52) U.S. Cl.
CPC .............. *C07C 55/22* (2013.01); *C07C 53/00* (2013.01); *C07C 55/02* (2013.01); *C07F 9/062* (2013.01); *C10M 105/32* (2013.01); *C10M 137/04* (2013.01)

(58) Field of Classification Search
CPC ......... C07C 55/22; C07C 53/00; C07C 55/02; C07F 9/062; C07F 9/106; C10M 105/32; C10M 105/38; C10M 2207/28; C10M 2207/2835; C10M 2207/345; C10M 169/04; C11C 3/00
See application file for complete search history.

(56) References Cited

U.S. PATENT DOCUMENTS

| | | | |
|---|---|---|---|
| 5,135,669 A | 8/1992 | Brois et al. | |
| 5,990,055 A * | 11/1999 | Garmier | C10M 169/042 508/491 |
| 2004/0235679 A1* | 11/2004 | Kurosky | C10M 169/00 508/174 |
| 2005/0055021 A1 | 3/2005 | Clement et al. | |
| 2009/0325830 A1* | 12/2009 | Schnur | C10M 163/00 508/186 |

(Continued)

FOREIGN PATENT DOCUMENTS

| | | |
|---|---|---|
| CN | 102395279 | 3/2012 |
| CN | 105475609 | 4/2016 |

(Continued)

OTHER PUBLICATIONS

"International Application Serial No. PCT US2019 030923, Invitation to Pay Additional Fees dated Jun. 19, 2019", 3 pgs.

(Continued)

*Primary Examiner* — Taiwo Oladapo
(74) *Attorney, Agent, or Firm* — Schwegman Lundberg & Woessner, P.A.

(57) ABSTRACT

A medical lubricant may comprise a base oil. The medical lubricant can be used on a surgical device.

20 Claims, 2 Drawing Sheets

(56) References Cited

U.S. PATENT DOCUMENTS

| | | | | |
|---|---|---|---|---|
| 2010/0298183 A1* | 11/2010 | Hiyoshi | ............... | C10M 129/72 |
| | | | | 508/202 |
| 2011/0160109 A1* | 6/2011 | Ruhr | ................ | C10M 173/025 |
| | | | | 508/428 |
| 2017/0049938 A1* | 2/2017 | Clement | ................ | A61L 31/10 |

FOREIGN PATENT DOCUMENTS

| | | |
|---|---|---|
| CN | 106085573 | 11/2016 |
| CN | 112513159 A | 3/2021 |
| EP | 1669093 | 6/2006 |
| EP | 2952101 | 12/2015 |
| EP | 3005878 | 4/2016 |
| JP | 2021523273 | 9/2021 |
| WO | 9601105 | 1/1996 |
| WO | 2017025900 | 2/2017 |
| WO | 2019217318 | 11/2019 |

OTHER PUBLICATIONS

"International Application Serial No. PCT US2019 030923, International Search Report dated Aug. 28, 2019", 4 pgs.

"International Application Serial No. PCT US2019 030923, Written Opinion dated Aug. 28, 2019", 7 pgs.

"European Application Serial No. 19800606.6, Extended European Search Report dated Oct. 11, 2021", 13 pgs.

"Chinese Application Serial No. 201980031246.6, Office Action dated Apr. 7, 2022", w English translation, 22 pgs.

Singh, S, "Multiple emulsion-based systems carrying insulin: development and characterization", Journal of Microencapsulation, Taylor and Francis, Basingstoke, GB, vol. 12, No. 6, (Nov. 1, 1995), 609-615.

* cited by examiner

MEDICAL LUBRICANT

CROSS-REFERENCE TO RELATED APPLICATION

This application claims the benefit of priority to U.S. Provisional Patent Application Ser. No. 62/667,778 entitled "MEDICAL LUBRICANT," filed May 7, 2018, the disclosure of which is incorporated herein in its entirety by reference.

BACKGROUND

Surgical processes often use cautery probes for cutting and/or cauterizing tissue. An example of a cautery probe is an electro-cautery probe, sometimes referred to as a tip, which is typically coated with a lubricant prior to and throughout the use of the electro-cautery probes to reduce charring. Improved lubricants to minimize charring and maintain the performance of the probe is desired.

Some lubricants include a lecithin, which contains a hydrophobic tail and hydrophilic head, similar in nature to the components of the cellular lipid bilayer or soap. This arrangement allows half of the molecule to embed in the aqueous cellular environment, leaving the hydrophobic head exposed, which does not bond to the surface of the surgical instrument, thus preventing the tissue from adhering to the instrument. This mechanism is effective but is limited by heat sensitivity. However, lecithin may be a relatively heat-sensitive compound, which may break down into a residue that does not retain its non-stick properties. As such, lecithin may degrade through the course of the intrinsically thermal process of electro-cautery. In addition, as the residue may build up on the probe, the transfer of energy from the probe to the tissue may become increasingly inefficient, resulting in longer burn-times. Furthermore, the charred residue may not remove easily, and so the further addition of fresh lubricant may not provide improved performance once the residue begins to accumulate. Improved lubricants may aid the surgical process.

SUMMARY

A medical lubricant may include a base oil. The medical lubricant can be used on a surgical device.

A formulation for a lubricant includes a base oil comprising a compound of the formula I:

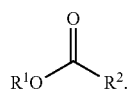

(I)

In formula I, $R^1$ is H, $C_1$-$C_6$ alkyl, $C_1$-$C_6$ alkenyl, or $C_1$-$C_6$ alkynyl, wherein each hydrogen atom in $C_1$-$C_6$ alkyl, $C_1$-$C_6$ alkenyl, or $C_1$-$C_6$ alkynyl is independently optionally substituted with halo, hydroxy, amino, oxo, or $OR^3$; $R^2$ is $C_{10}$-$C_{25}$ alkyl, $C_{10}$-$C_{25}$ alkenyl, or $C_{10}$-$C_{25}$ alkynyl, and wherein each hydrogen atom in $C_{10}$-$C_{25}$ alkyl, $C_{10}$-$C_{25}$ alkenyl, or $C_{10}$-$C_{25}$ alkynyl is independently optionally substituted with halo, hydroxy, amino, oxo, or $OR^7$; or a salt thereof. The formulation may further include a phospholipid; or a salt thereof; and a salt of the formula $M^1$ ($R^8$)($R^9$) (II). $M^1$ can be a divalent cation, $R^7$ and $R^8$ are independently $OC(O)C_{10}$-$C_{25}$ alkyl, $^-OC(O)C_{10}$-$C_{25}$ alkenyl, or $^-OC(O)C_{10}$-$C_{25}$ alkynyl, and wherein each hydrogen atom in $C_{10}$-$C_{25}$ alkyl, $C_{10}$-$C_{25}$ alkenyl, or $C_{10}$-$C_{25}$ alkynyl is independently optionally substituted with halo, hydroxy, amino, oxo, or $OR^{10}$. Each of $R^3$, $R^7$, and $R^{10}$ is independently H, $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, —C(O)$C_1$-$C_6$ alkyl, —C(O)$C_1$-$C_6$ alkenyl, —C(O)$C_1$-$C_6$ alkynyl, —C(O)$C_{10}$-$C_{25}$ alkyl, —C(O)$C_{10}$-$C_{25}$ alkenyl, —C(O)$C_{10}$-$C_{25}$ alkynyl, wherein each hydrogen atom in $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, —C(O)$C_1$-$C_6$ alkyl, —C(O)$C_1$-$C_6$ alkenyl, —C(O)$C_1$-$C_6$ alkynyl, —C(O)$C_{10}$-$C_{25}$ alkyl, —C(O)$C_{10}$-$C_{25}$ alkenyl, —C(O)$C_{10}$-$C_{25}$ alkynyl is independently optionally substituted with halo, hydroxy, or amino.

A method of coating an electrocautery device includes contacting a surface of the electrocautery device with a formulation. The formulation includes a base oil comprising a compound of the formula I:

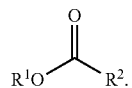

(I)

In formula I, $R^1$ is H, $C_1$-$C_6$ alkyl, $C_1$-$C_6$ alkenyl, or $C_1$-$C_6$ alkynyl, wherein each hydrogen atom in $C_1$-$C_6$ alkyl, $C_1$-$C_6$ alkenyl, or $C_1$-$C_6$ alkynyl is independently optionally substituted with halo, hydroxy, amino, oxo, or $OR^3$; $R^2$ is $C_{10}$-$C_{25}$ alkyl, $C_{10}$-$C_{25}$ alkenyl, or $C_{10}$-$C_{25}$ alkynyl, and wherein each hydrogen atom in $C_{10}$-$C_{25}$ alkyl, $C_{10}$-$C_{25}$ alkenyl, or $C_{10}$-$C_{25}$ alkynyl is independently optionally substituted with halo, hydroxy, amino, oxo, or $OR^7$; or a salt thereof. The formulation may further include a phospholipid; or a salt thereof; and a salt of the formula $M^1$ ($R^8$)($R^9$) (II). $M^1$ can be a divalent cation, $R^7$ and $R^8$ are independently $^-OC(O)C_{10}$-$C_{25}$ alkyl, $^-OC(O)C_{10}$-$C_{25}$ alkenyl, or $^-OC(O)C_{10}$-$C_{25}$ alkynyl, and wherein each hydrogen atom in $C_{10}$-$C_{25}$ alkyl, $C_{10}$-$C_{25}$ alkenyl, or $C_{10}$-$C_{25}$ alkynyl is independently optionally substituted with halo, hydroxy, amino, oxo, or $OR^{10}$. Each of $R^3$, $R^7$, and $R^{10}$ is independently H, $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, —C(O)$C_1$-$C_6$ alkyl, —C(O)$C_1$-$C_6$ alkenyl, —C(O)$C_1$-$C_6$ alkynyl, —C(O)$C_{10}$-$C_{25}$ alkyl, —C(O)$C_{10}$-$C_{25}$ alkenyl, —C(O)$C_{10}$-$C_{25}$ alkynyl, wherein each hydrogen atom in $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, —C(O)$C_1$-$C_6$ alkyl, —C(O)$C_1$-$C_6$ alkenyl, —C(O)$C_1$-$C_6$ alkynyl, —C(O)$C_{10}$-$C_{25}$ alkyl, —C(O)$C_{10}$-$C_{25}$ alkenyl, —C(O)$C_{10}$-$C_{25}$ alkynyl is independently optionally substituted with halo, hydroxy, or amino.

A method of preparing a formulation is disclosed. The formulation includes a base oil comprising a compound of the formula I:

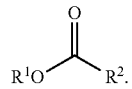

(I)

In formula I, $R^1$ is H, $C_1$-$C_6$ alkyl, $C_1$-$C_6$ alkenyl, or $C_1$-$C_6$ alkynyl, wherein each hydrogen atom in $C_1$-$C_6$ alkyl, $C_1$-$C_6$ alkenyl, or $C_1$-$C_6$ alkynyl is independently optionally substituted with halo, hydroxy, amino, oxo, or $OR^3$; $R^2$ is $C_{10}$-$C_{25}$ alkyl, $C_{10}$-$C_{25}$ alkenyl, or $C_{10}$-$C_{25}$ alkynyl, and wherein each hydrogen atom in $C_{10}$-$C_{25}$ alkyl, $C_{10}$-$C_{25}$ alkenyl, or $C_{10}$-$C_{25}$ alkynyl is independently optionally substituted with halo, hydroxy, amino, oxo, or $OR^7$; or a salt thereof. The formulation may further include a phospholipid; or a salt thereof; and a salt of the formula $M^1(R^8)(R^9)$ (II). $M^1$ can be a divalent cation, $R^7$ and $R^8$ are independently $^-OC(O)C_{10}$-$C_{25}$ alkyl, $^-OC(O)C_{10}$-$C_{25}$ alkenyl, or $^-OC(O)C_{10}$-$C_{25}$ alkynyl, and wherein each hydrogen atom in $C_{10}$-$C_{25}$ alkyl, $C_{10}$-$C_{25}$ alkenyl, or $C_{10}$-$C_{25}$ alkynyl is independently optionally substituted with halo, hydroxy, amino, oxo, or $OR^{10}$. Each of $R^3$, $R^7$, and $R^{10}$ is independently H, $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, —$C(O)C_1$-$C_6$ alkyl, —$C(O)C_1$-$C_6$ alkenyl, —$C(O)C_1$-$C_6$ alkynyl, —$C(O)C_{10}$-$C_{25}$ alkyl, —$C(O)C_{10}$-$C_{25}$ alkenyl, —$C(O)C_{10}$-$C_{25}$ alkynyl, wherein each hydrogen atom in $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, —$C(O)C_1$-$C_6$ alkyl, —$C(O)C_1$-$C_6$ alkenyl, —$C(O)C_1$-$C_6$ alkynyl, —$C(O)C_{10}$-$C_{25}$ alkyl, —$C(O)C_{10}$-$C_{25}$ alkenyl, —$C(O)C_{10}$-$C_{25}$ alkynyl is independently optionally substituted with halo, hydroxy, or amino. The formulation further includes a compound of formula V

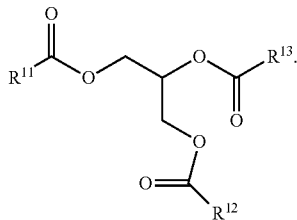

(V)

In formula V, each of $R^{11}$, $R^2$, and $R^3$ is independently $C_{10}$-$C_{25}$ alkyl, $C_{10}$-$C_{25}$ alkenyl, or $C_{10}$-$C_{25}$ alkynyl, and wherein each hydrogen atom in $C_{10}$-$C_{25}$ alkyl, $C_{10}$-$C_{25}$ alkenyl, or $C_{10}$-$C_{25}$ alkynyl is independently optionally substituted with halo, hydroxy, amino, oxo, or $OR^{14}$. $R^{14}$ is H, $C_1$-$C_6$ alkyl, $C_1$-$C_6$ alkenyl, or $C_1$-$C_6$ alkynyl, wherein each hydrogen atom in $C_1$-$C_6$ alkyl, $C_1$-$C_6$ alkenyl, and $C_1$-$C_6$ alkynyl is independently optionally substituted with a halo, hydroxy, or an amino, a long chain alcohol, a saturated fatty acid, a mixture thereof, or salts thereof. The method includes mixing the base oil with the compound of formula V and mixing the base oil with a phospholipid.

A kit includes formulation for a lubricant that includes a base oil comprising a compound of the formula I:

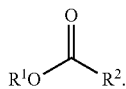

(I)

In formula I, $R^1$ is H, $C_1$-$C_6$ alkyl, $C_1$-$C_6$ alkenyl, or $C_1$-$C_6$ alkynyl, wherein each hydrogen atom in $C_1$-$C_6$ alkyl, $C_1$-$C_6$ alkenyl, or $C_1$-$C_6$ alkynyl is independently optionally substituted with halo, hydroxy, amino, oxo, or $OR^3$; $R^2$ is $C_{10}$-$C_{25}$ alkyl, $C_{10}$-$C_{25}$ alkenyl, or $C_{10}$-$C_{25}$ alkynyl, and wherein each hydrogen atom in $C_{10}$-$C_{25}$ alkyl, $C_{10}$-$C_{25}$ alkenyl, or $C_{10}$-$C_{25}$ alkynyl is independently optionally substituted with halo, hydroxy, amino, oxo, or $OR^7$; or a salt thereof. The formulation may further include a phospholipid; or a salt thereof; and a salt of the formula $M^1(R^8)(R^9)$ (II). $M^1$ can be a divalent cation, $R^7$ and $R^8$ are independently $^-OC(O)C_{10}$-$C_{25}$ alkyl, $^-OC(O)C_{10}$-$C_{25}$ alkenyl, or $^-OC(O)C_{10}$-$C_{25}$ alkynyl, and wherein each hydrogen atom in $C_{10}$-$C_{25}$ alkyl, $C_{10}$-$C_{25}$ alkenyl, or $C_{10}$-$C_{25}$ alkynyl is independently optionally substituted with halo, hydroxy, amino, oxo, or $OR^{10}$. Each of $R^3$, $R^7$, and $R^{10}$ is independently H, $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, —$C(O)C_1$-$C_6$ alkyl, —$C(O)C_1$-$C_6$ alkenyl, —$C(O)C_1$-$C_6$ alkynyl, —$C(O)C_{10}$-$C_{25}$ alkyl, —$C(O)C_{10}$-$C_{25}$ alkenyl, —$C(O)C_{10}$-$C_{25}$ alkynyl, wherein each hydrogen atom in $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, —$C(O)C_1$-$C_6$ alkyl, —$C(O)C_1$-$C_6$ alkenyl, —$C(O)C_1$-$C_6$ alkynyl, —$C(O)C_{10}$-$C_{25}$ alkyl, —$C(O)C_{10}$-$C_{25}$ alkenyl, —$C(O)C_{10}$-$C_{25}$ alkynyl is independently optionally substituted with halo, hydroxy, or amino. The kit further includes a cautery probe.

A method of cauterization includes applying a formulation to a cautery probe and cauterizing tissue with the cautery probe. The formulation includes a base oil comprising a compound of the formula I:

(I)

In formula I, $R^1$ is H, $C_1$-$C_6$ alkyl, $C_1$-$C_6$ alkenyl, or $C_1$-$C_6$ alkynyl, wherein each hydrogen atom in $C_1$-$C_6$ alkyl, $C_1$-$C_6$ alkenyl, or $C_1$-$C_6$ alkynyl is independently optionally substituted with halo, hydroxy, amino, oxo, or $OR^3$; $R^2$ is $C_{10}$-$C_{25}$ alkyl, $C_{10}$-$C_{25}$ alkenyl, or $C_{10}$-$C_{25}$ alkynyl, and wherein each hydrogen atom in $C_{10}$-$C_{25}$ alkyl, $C_{10}$-$C_{25}$ alkenyl, or $C_{10}$-$C_{25}$ alkynyl is independently optionally substituted with halo, hydroxy, amino, oxo, or $OR^7$; or a salt thereof. The formulation may further include a phospholipid; or a salt thereof; and a salt of the formula $M^1(R^8)(R^9)$ (II). $M^1$ can be a divalent cation, $R^7$ and $R^8$ are independently $^-OC(O)C_{10}$-$C_{25}$ alkyl, —$OC(O)C_{10}$-$C_{25}$ alkenyl, or $^-OC(O)C_{10}$-$C_{25}$ alkynyl, and wherein each hydrogen atom in $C_{10}$-$C_{25}$ alkyl, $C_{10}$-$C_{25}$ alkenyl, or $C_{10}$-$C_{25}$ alkynyl is independently optionally substituted with halo, hydroxy, amino, oxo, or $OR^{10}$. Each of $R^3$, $R^7$, and $R^{10}$ is independently H, $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, —$C(O)C_1$-$C_6$ alkyl, —$C(O)C_1$-$C_6$ alkenyl, —$C(O)C_1$-$C_6$ alkynyl, —$C(O)C_{10}$-$C_{25}$ alkyl, —$C(O)C_{10}$-$C_{25}$ alkenyl, —$C(O)C_{10}$-$C_{25}$ alkynyl, wherein each hydrogen atom in $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, —$C(O)C_1$-$C_6$ alkyl, —$C(O)C_1$-$C_6$ alkenyl, —$C(O)C_1$-$C_6$ alkynyl, —$C(O)C_{10}$-$C_{25}$ alkyl, —$C(O)C_{10}$-$C_{25}$ alkenyl, —$C(O)C_{10}$-$C_{25}$ alkynyl is independently optionally substituted with halo, hydroxy, or amino. The kit further includes a cautery probe.

BRIEF DESCRIPTION OF THE DRAWINGS

FIG. 2A shows the burn marks on a tissue left from the probes coated in a comparative lubricant and a lubricant according to the present disclosure. FIG. 2B shows a representative application of a lubricant according to the present disclosure on a fresh tip. FIG. 2C shows a representative sample of tissue-cling from the comparative lubricant. FIG. 2D shows a representative sample of tissue-cling from a lubricant according to the present disclosure. FIG. 2E shows a characteristic example of burns using a lubricant according to the present disclosure. And FIG. 2F shows a representative example of a used probe coated in a depleted lubricant according to the present disclosure.

DETAILED DESCRIPTION

Figure 1:
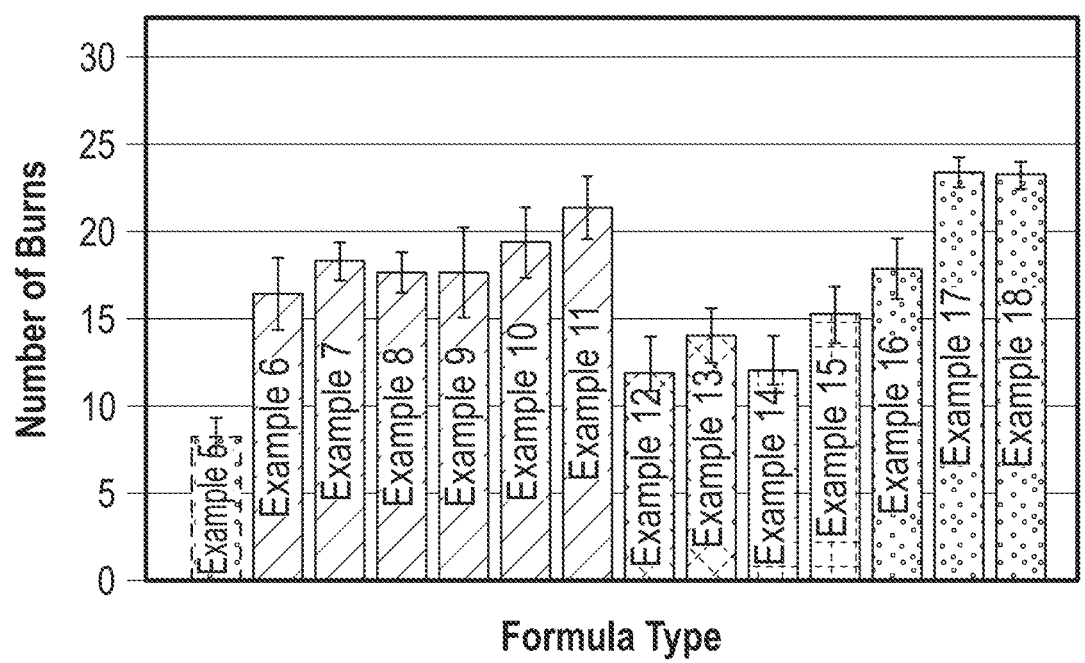
FIG. 1 shows the number of burns achieved using different lubricants described in the Examples.

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{20}$, $C_{10}$-$C_{20}$, $C_1$-$C_6$, and $C_1$-$C_4$. Illustratively, such particularly limited length alkyl groups, including $C_1$-$C_8$, $C_1$-$C_7$, $C_1$-$C_6$, and $C_1$-$C_4$, and the like may be referred to as "lower alkyl." In some embodiments, alkyl may be $C_6$-$C_{10}$, $C_{11}$-$C_{16}$, $C_{16}$-$C_{20}$, and $C_6$-$C_{20}$. Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, nonyl, decyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, oxo, (=O), thiocarbonyl, O-carbamyl, N-carbamyl, O-thiocarbamyl, N-thiocarbamyl, C-amido, N-amido, C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, and the like.

As used herein, the term "alkylene" refers to a divalent -alkyl- group in which alkyl is as defined previously. Exemplary alkylene groups include —$CH_2$—, —$(CH_2)_2$— and —$C(CH_3)HCH_2$—.

As used herein, the term "alkenyl" includes a chain of carbon atoms, which is optionally branched, and contains from 2 to 20 carbon atoms, and also includes at least one carbon-carbon double bond (i.e. C=C). It will be understood that in certain embodiments, alkenyl may be advantageously of limited length, including $C_2$-$C_{20}$, $C_{10}$-$C_{20}$, $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkenyl groups, including $C_2$-$C_8$, $C_2$-$C_7$, $C_2$-$C_6$, and $C_2$-$C_4$ may be referred to as lower alkenyl. In some embodiments, alkenyl may be $C_6$-$C_{10}$, $C_{11}$-$C_{16}$, $C_6$-$C_{20}$, and $C_6$-$C_{20}$. Alkenyl may be unsubstituted or substituted as described for alkyl or as described in the various embodiments provided herein. Illustrative alkenyl groups include, but are not limited to, ethenyl, 1-propenyl, 2-propenyl, 1-, 2-, or 3-butenyl, and the like.

As used herein, the term "alkenylene" refers to a divalent -alkenyl- group in which alkenyl is as defined previously. Exemplary alkenylene groups include —CH=CH—, —CH=CHCH$_2$—, and —CH$_2$CH=CH—.

As used herein, the term "alkynyl" includes a chain of carbon atoms, which is optionally branched, and contains from 2 to 20 carbon atoms, and includes at least one carbon-carbon triple bond (i.e. C≡C). It will be understood that in certain embodiments alkynyl may each be advantageously of limited length, including $C_2$-$C_{20}$, $C_{10}$-$C_{20}$, $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkynyl groups, including $C_2$-$C_8$, $C_2$-$C_7$, $C_2$-$C_6$, and $C_2$-$C_4$ may be referred to as lower alkynyl. In some embodiments, alkynyl may be $C_6$-$C_{10}$, $C_{11}$-$C_{16}$, $C_{16}$-$C_{20}$, and $C_6$-$C_{20}$. Alkynyl may be unsubstituted or substituted as described for alkyl or as described in the various embodiments provided herein. Illustrative alkynyl groups include, but are not limited to, ethynyl, 1-propynyl, 2-propynyl, 1-, 2-, or 3-butynyl, and the like.

As used herein, the term "alkynylene" refers to a divalent -alkynyl- group in which -alkynyl- is as defined previously. Exemplary alkynylene groups include ethynyl and propargyl.

As used herein, the term "aryl" refers to an all-carbon monocyclic or fused-ring polycyclic groups of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthalenyl, and anthracenyl. The aryl group may be unsubstituted or substituted as described for alkyl or as described in the various embodiments provided herein.

As used herein, the term "arylene" refers to a divalent -aryl- group in which aryl is as defined previously. Exemplary arylene groups include -phenylene- and -napthalenylene-.

As used herein, the term "cycloalkyl" refers to a 3 to 15 member all-carbon monocyclic ring, an all-carbon 5-member/6-member or 6-member/6-member fused bicyclic ring, or a multicyclic fused ring (a "fused" ring system means that each ring in the system shares an adjacent pair of carbon atoms with each other ring in the system) group where one or more of the rings may contain one or more double bonds but the cycloalkyl does not contain a completely conjugated pi-electron system. It will be understood that in certain embodiments, cycloalkyl may be advantageously of limited size such as $C_3$-$C_{13}$, $C_3$-$C_6$, $C_3$-$C_6$ and $C_4$-$C_6$. The cycloalkyl may be unsubstituted or substituted as described for alkyl or as described in the various embodiments provided herein. Illustrative cycloalkyl groups include, but are not limited to, cyclopropyl, cyclobutyl, cyclopentyl, cyclopentenyl, cyclopentadienyl, cyclohexyl, cyclohexenyl, cycloheptyl, adamantyl, norbornyl, norbornenyl, 9H-fluoren-9-yl, and the like.

As used herein, the term "cycloalkylene" refers to a divalent -cycloalkyl- group in which cycloalkyl is as defined previously. Exemplary cycloalkylene groups include -cyclohexylene- and -cylcopentylene-.

In accordance with the invention, the term "heteroalkyl" includes a chain of atoms that includes both carbon and at least one heteroatom, and is optionally branched. It is to be further understood that in certain embodiments, heteroalkyl may be advantageously of limited length, including $C_1$-$C_{20}$, $C_{10}$-$C_{20}$, $C_1$-$C_{12}$, $C_1$-$C_{10}$, $C_1$-$C_9$, $C_1$-$C_8$, $C_1$-$C_7$, $C_1$-$C_6$, and $C_1$-$C_4$. Illustratively, such particularly limited length heteroalkyl groups, including $C_1$-$C_8$, $C_1$-$C_7$, $C_1$-$C_6$, and $C_1$-$C_4$, and the like may be referred to as "lower heteroalkyl." In some embodiments, heteroalkyl may be $C_6$-$C_{10}$, $C_{11}$-$C_{16}$, $C_{16}$-$C_{20}$, and $C_6$-$C_{20}$. Illustrative heteroatoms include nitrogen, oxygen, and sulfur. In certain variations, illustrative heteroatoms also include phosphorus and selenium.

As used herein, the term "heteroalkylene" refers to a divalent -heteroalkyl- group in which heteroalkyl is as defined previously. Exemplary heteroalkylene groups include -ethoxylene-.

As used herein, the term "heteroalkenyl" includes both a chain of carbon atoms which is optionally branched and at least one heteroatom, and also includes at least one carbon-carbon double bond (i.e. C=C). It will be understood that in certain embodiments, heteroalkenyl may be advantageously of limited length, including $C_2$-$C_{20}$, $C_{10}$-$C_{20}$, $C_2$-$C_{12}$, $C_2$-$C_9$, $C_2$-$C_8$, $C_2$-$C_7$, $C_2$-$C_6$, and $C_2$-$C_4$. Illustratively, such particularly limited length heteroalkenyl groups, including $C_2$-$C_8$, $C_2$-$C_7$, $C_2$-$C_6$, and $C_2$-$C_4$ may be referred to as lower heteroalkenyl. In some embodiments, heteroalkenyl may be $C_6$-$C_{10}$, $C_{16}$-$C_{20}$, and $C_6$-$C_{20}$.

Heteroalkenyl may be unsubstituted or substituted as described for alkyl or as described in the various embodiments provided herein. Illustrative heteroatoms include nitrogen, oxygen, and sulfur. In certain variations, illustrative heteroatoms also include phosphorus and selenium.

As used herein, the term "heteroalkynyl" includes both a chain of carbon atoms which is optionally branched and at least one heteroatom and also includes at least one carbon-carbon double bond (i.e. CC). It will be understood that in certain embodiments, heteroalkynyl may be advantageously of limited length, including $C_2$-$C_{20}$, $C_{10}$-$C_{20}$, $C_2$-$C_{12}$, $C_2$-$C_9$, $C_2$-$C_8$, $C_2$-$C_7$, $C_2$-$C_6$, and $C_2$-$C_4$. Illustratively, such particularly limited length heteroalkynyl groups, including $C_2$-$C_8$, $C_2$-$C_7$, $C_2$-$C_6$, and $C_2$-$C_4$ may be referred to as lower heteroalkynyl. In some embodiments, heteroalkynyl may be $C_6$-$C_{10}$, $C_{11}$-$C_{16}$, $C_{16}$-$C_{20}$, and $C_6$-$C_{20}$. Heteroalkynyl may be unsubstituted or substituted as described for alkyl or as described in the various embodiments provided herein. Illustrative heteroatoms include nitrogen, oxygen, and sulfur. In certain variations, illustrative heteroatoms also include phosphorus and selenium.

As used herein, the term "heteroalkynylene" refers to a divalent -heteroalkynyl- group in which heteroalkynyl is as defined previously.

As used herein, the term "cycloheteroalkyl" including heterocyclyl and heterocycle, includes a chain of atoms that includes both carbon, such as heteroalkyl, and at least one heteroatom, and is optionally branched, where at least a portion of the chain is cyclic. Illustrative heteroatoms include nitrogen, oxygen, and sulfur. In certain variations, illustrative heteroatoms also include phosphorus and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like. As used herein, the term "heterocycloalkyl" refers to a monocyclic or fused ring group having in the ring(s) from 3 to 12 ring atoms, in which at least one ring atom is a heteroatom, such as nitrogen, oxygen or sulfur, the remaining ring atoms being carbon atoms. Heterocycloalkyl may optionally contain 1, 2, 3 or 4 heteroatoms. Heterocycloalkyl may also have one or more double bonds, including double bonds to nitrogen (e.g. C=N or N=N) but does not contain a completely conjugated pi-electron system. It will be understood that in certain embodiments, heterocycloalkyl may be advantageously of limited size such as 3- to 7-membered heterocycloalkyl, 5- to 7-membered heterocycloalkyl, and the like. Heterocycloalkyl may be unsubstituted or substituted as described for alkyl or as described in the various embodiments provided herein. Illustrative heterocycloalkyl groups include, but are not limited to, oxiranyl, thianaryl, azetidinyl, oxetanyl, tetrahydrofuranyl, pyrrolidinyl, tetrahydropyranyl, piperidinyl, 1,4-dioxanyl, morpholinyl, 1,4-dithianyl, piperazinyl, oxepanyl, 3,4-dihydro-2H-pyranyl, 5,6-dihydro-2H-pyranyl, 2H-pyranyl, 1, 2, 3, 4-tetrahydropyridinyl, and the like.

As used herein, the term "cycloheteroalkylene" refers to a divalent -cycloheteroalkyl- group in which cycloheteroalkyl is as defined previously. Exemplary cycloheteroalkylene groups include -morpholinylene- and -piperazinylene-.

As used herein, the term "heteroaryl" refers to a monocyclic or fused ring group of 5 to 12 ring atoms containing one, two, three, or four ring heteroatoms selected from nitrogen, oxygen, and sulfur, the remaining ring atoms being carbon atoms, and also having a completely conjugated pi-electron system. It will be understood that in certain embodiments, heteroaryl may be advantageously of limited size such as 3- to 7-membered heteroaryl, 5- to 7-membered heteroaryl, and the like. Heteroaryl may be unsubstituted or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, carbazoloyl, and the like.

As used herein, the term "heteroarylene" refers to a divalent -heteroaryl- group in which heteroaryl is as defined previously. Exemplary heteroarylene groups include -imidazoylene- and -furanylene-.

As used herein, "hydroxy" or "hydroxyl" refers to an —OH group.

As used herein, "alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

As used herein, "halo" or "halogen" refers to fluorine, chlorine, bromine or iodine.

As used herein, "bond" refers to a covalent bond.

As used herein, "amino" refers to an —NR"R" group, where R" is any R group as described in the various embodiments provided herein.

As used herein, "optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may, but need not be present, and the description includes situations where the heterocycle group is substituted with an alkyl group and situations where the heterocycle group is not substituted with the alkyl group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

For the purposes of promoting an understanding of the principles of the disclosure, reference will now be made to a number of illustrative embodiments illustrated in the drawings and specific language will be used to describe the same.

Lubricants may be used in medical procedures, such as cauterization, to reduce the build-up of material on cautery probes. Illustrative cautery probes include electrocautery probes, heated scalpels, and those capable for use in robotic procedures. Illustrative embodiments of a lubricant may comprise a formulation comprising a base oil, a phospholipid, a salt, or a combination thereof. In some embodiments, a lubricant in accordance with the present disclosure uses a multi-phase non-stick mechanism. In some embodiments, the lubricant more than doubles the number of electrocautery burns per application compared to a comparative lubricant before the lubricant is exhausted and tissue sticking begins to occur (see FIG. 1). Additionally, in some embodiments, a lubricant may retain a transparent appearance during use, preventing the tissue discoloration noted with a comparative lubricant formula (see FIG. 2A). In some embodiments, the formulation also comprises natural fragrance oils, which assist in offsetting a foul odor that can be generated by the electrocautery process.

The formulation for a lubricant may comprise a certain percentage of a base oil. The percentage of the base oil for the formulation for a lubricant may be at least about 40%, at least about 50%, at least about 60%, or at least about 65% by weight of the formulation. In some embodiments, the base oil is about 40%, about 45%, about 50%, about 55%, about 60%, about 65%, about 70%, about 75%, about 80%, about 85%, about 90%, or about 95% by weight of the formulation. In some embodiments, the base oil is about 40% to about 95%, about 50% to about 95%, about 55% to about 95%, about 55% to about 90%, about 60% to about 95%, or about 60% to about 90% by weight of the formulation. In some embodiments, the formulation may comprise one, two, or three base oils. In some embodiments, the formulation comprises a mixture of base oils.

In some illustrative embodiments, the base oil comprises a compound of the formula I

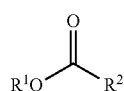
(I)

or a salt thereof. In some embodiments, $R^1$ is H, $C_1$-$C_6$ alkyl, $C_1$-$C_6$ alkenyl, or $C_1$-$C_6$ alkynyl. Illustratively, each hydrogen atom in $C_1$-$C_6$ alkyl, $C_1$-$C_6$ alkenyl, or $C_1$-$C_6$ alkynyl is independently optionally substituted with halo, hydroxy, amino, oxo, or $OR^3$. In some embodiments, $R^2$ is $C_{10}$-$C_{25}$ alkyl, $C_{10}$-$C_{25}$ alkenyl, or $C_{10}$-$C_{25}$ alkynyl, wherein each hydrogen atom in $C_{10}$-$C_{25}$ alkyl, $C_{10}$-$C_{25}$ alkenyl, or $C_{10}$-$C_{25}$ alkynyl is independently optionally substituted with halo, hydroxy, amino, oxo, or $OR^7$. In some embodiments, each of $R^3$ and $R^7$ is independently H, $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, —C(O)$C_1$-$C_6$ alkyl, —C(O)$C_1$-$C_6$ alkenyl, —C(O)$C_1$-$C_6$ alkynyl, —C(O)$C_{10}$-$C_{25}$ alkyl, —C(O)$C_{10}$-$C_{25}$ alkenyl, —C(O)$C_{10}$-$C_{25}$ alkynyl, and wherein each hydrogen atom in $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, —C(O)$C_1$-$C_6$ alkyl, —C(O)$C_1$-$C_6$ alkenyl, —C(O)$C_1$-$C_6$ alkynyl, —C(O)$C_{10}$-$C_{25}$ alkyl, —C(O)$C_{10}$-$C_{25}$ alkenyl, —C(O)$C_{10}$-$C_{25}$ alkynyl is independently optionally substituted with halo, hydroxy, or amino or a salt thereof.

In some embodiments, $R^1$ is H and the compound of formula I is a carboxylic acid. In some embodiments, $R^1$ is an optionally substituted $C_1$-$C_6$ alkyl, and the compound of formula I is an ester. Optional substitutions of the $C_1$-$C_6$ alkyl include halo, hydroxy, amino, oxo, or $OR^3$. In some embodiments each $R^3$ is independently H, $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, —C(O)$C_1$-$C_6$ alkyl, —C(O)$C_1$-$C_6$ alkenyl, —C(O)$C_1$-$C_6$ alkynyl, —C(O)$C_{10}$-$C_{25}$ alkyl, —C(O)$C_{10}$-$C_{25}$ alkenyl, or —C(O)$C_{10}$-$C_{25}$ alkynyl, wherein each hydrogen atom in $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, —C(O)$C_1$-$C_6$ alkyl, —C(O)$C_1$-$C_6$ alkenyl, —C(O)$C_1$-$C_6$ alkynyl, —C(O)$C_{10}$-$C_{25}$ alkyl, —C(O)$C_{10}$-$C_{25}$ alkenyl, and —C(O)$C_{10}$-$C_{25}$ alkynyl is independently optionally substituted with halo, hydroxy, or amino.

In some embodiments, each $R^3$ is independently —C(O)$C_1$-$C_6$ alkyl, —C(O)$C_1$-$C_6$ alkenyl, —C(O)$C_1$-$C_6$ alkynyl, —C(O)$C_{10}$-$C_{25}$ alkyl, —C(O)$C_{10}$-$C_{25}$ alkenyl, —C(O)$C_{10}$-$C_{25}$ alkynyl, wherein each hydrogen atom in —C(O)$C_1$-$C_6$ alkyl, —C(O)$C_1$-$C_6$ alkenyl, —C(O)$C_1$-$C_6$ alkynyl, —C(O)$C_{10}$-$C_{25}$ alkyl, —C(O)$C_{10}$-$C_{25}$ alkenyl, and —C(O)$C_{10}$-$C_{25}$ alkynyl is independently optionally substituted with halo, hydroxy, or amino. In some other embodiments, each $R^3$ is independently —C(O)$C_{10}$-$C_{25}$ alkyl, —C(O)$C_{10}$-$C_{25}$ alkenyl, —C(O)$C_{10}$-$C_{25}$ alkynyl, wherein each hydrogen atom in —C(O)$C_{10}$-$C_{25}$ alkyl, —C(O)$C_{10}$-$C_{25}$ alkenyl, and —C(O)$C_{10}$-$C_{25}$ alkynyl is independently optionally substituted with halo, hydroxy, or amino.

In some embodiments, the compound of formula I is triolein. In some embodiments, the compound of formula I is trimyristicin or isopropyl myristate. In some embodiments, the compound of formula I is derived from avocado oil, canola oil, castor oil, coconut oil, olive oil, palm oil, safflower oil, or sunflower, high-oleic oil. In some embodiments, the formulation comprises more than one compound of formula I. In some embodiments, the formulation comprises two or at least two compounds of formula I.

The base oil may comprise a certain percentage of the compound of formula I. The percentage of the compound of formula I in the base oil may be at least about 10%, at least about 20%, at least about 30%, at least about 40%, or at least about 50% by weight of the base oil. In some embodiments, the compound of formula I is about 10%, about 15%, about 20%, about 25%, about 30%, about 35%, about 40%, about 45%, about 50%, about 55%, about 60%, about 65%, about 75%, about 85%, about 90%, or about 100% by weight of the base oil. In some embodiments, the compound of formula I is about 10% to about 100%, about 30% to about 100%, about 30% to about 85%, about 35% to about 85%, about 45% to about 85%, or about 50% to about 75% by weight of the base oil.

In some embodiments, the base oil may be a vegetable oil. In some other embodiments, the base oil may be a lecithin. In some embodiments, the base oil may be selected from the group consisting of avocado oil, grapeseed oil, canola oil, coconut oil, castor oil, olive oil, palm oil, safflower oil, sunflower oil, and triolein. The base oil may comprise fatty acids that are unsaturated, saturated, or polyunsaturated. In some embodiments, the base oil is avocado oil. In some embodiments, the base oil is grape seed oil.

According to some aspects of the present disclosure, the base oil has a smoke point. In some embodiments, the smoke point of the base oil is at least about 380° F., at least about 400° F., at least about 425° F., at least about 450° F., at least about 475° F., at least about 490° F., at least about 500° F., or at least about 510° F. In some embodiments, the base oil has a smoke point less than about 900° F., less than about 800° F., or less than about 750° F. In some embodiments, the base oil has a smoke point in a range of about 380° F. to about 900° F., about 380° F. to about 750° F., about 380° F. to about 650° F., about 400° F. to about 650° F., or about 400° F. to about 550° F. In some embodiments, the base oil is avocado oil (smoke point about 520° F.), canola oil (smoke point about 430° F.), coconut oil (smoke point about 400° F.), castor oil (smoke point about 390° F.), olive oil (smoke point about 410-460° F.), palm oil (smoke point about 450° F.), safflower oil (smoke point about 450° F.), or sunflower, high-oleic oil (smoke point about 450° F.). In some embodiments, the base oil is isopropyl myristate.

In some embodiments, the formulation for the lubricant comprises a phospholipid or an equivalent thereof. Illustratively, the phospholipid comprises a lecithin, a choline, lipid, or a combination thereof. In some embodiments, the lipid is hydrogenated. In some embodiments, the lecithin has been processed by acetylation, hydrogenation, phosphatidyl choline enrichment, or a combination thereof to improve heat resistance. In some embodiments, the lecithin is in the form of a liquid or a solid.

In some illustrative embodiments, the phospholipid comprises a compound according to formula IV

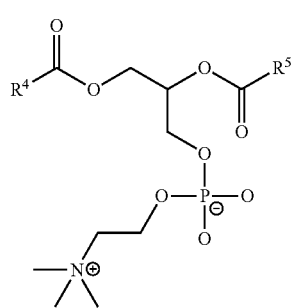

(IV)

or a salt thereof. In some embodiments, each of $R^4$ and $R^5$ is independently $C_{10}$-$C_{25}$ alkyl, $C_{10}$-$C_{25}$ alkenyl, or $C_{10}$-$C_{25}$ alkynyl, and each hydrogen atom in $C_{10}$-$C_{25}$ alkyl, $C_{10}$-$C_{25}$ alkenyl, and $C_{10}$-$C_{25}$ alkynyl is independently optionally substituted with halo, hydroxy, amino, oxo, or $OR^6$. In illustrative embodiments, $R^6$ is H, $C_1$-$C_6$ alkyl, $C_1$-$C_6$ alkenyl, or $C_1$-$C_6$ alkynyl, and wherein each hydrogen atom in $C_1$-$C_6$ alkyl, $C_1$-$C_6$ alkenyl, and $C_1$-$C_6$ alkynyl is independently optionally substituted with halo, hydroxy, or amino. In some embodiments, the phospholipid or a salt thereof comprises at least one $C_{10}$-$C_{25}$ alkyl. In some embodiments, the phospholipid or a salt thereof is substantially free from a $C_{10}$-$C_{25}$ alkenyl.

The formulation for a lubricant may comprise a certain percentage of a phospholipid or salt thereof. The percentage of phospholipid or salt thereof for the formulation for a lubricant may be at least about 2%, at least about 3%, at least about 4%, or at least about 5% by weight of the formulation. In some embodiments, the phospholipid or salt thereof may be less than about 20%, less than about 15%, or less than about 10% by weight of the formulation. In some embodiments, the phospholipid or salt thereof is about 2%, about 3%, about 4%, about 5%, about 6%, about 7%, about 8%, about 9%, about 10%, about 12%, about 15%, or about 20% by weight of the formulation. In some embodiments, the phospholipid or salt thereof is about 2% to about 20%, about 2% to about 15%, about 3% to about 15%, about 3% to about 10%, or about 4% to about 10% by weight of the formulation.

In some embodiments, the formulation comprises a component that may promote or participate in the formation of a non-stick surface on the probe. In some embodiments, this component may be suspended in the formulation. In some embodiments, the formulation for the lubricant comprises a salt of the formula $$M^1(R^8)(R^9)(\text{calcium stearate}) \quad \text{(II)}.$$

In some embodiments, $M^1$ is a divalent cation. In some embodiments, $R^7$ and $R^8$ are independently $^-OC(O)C_{10}$-$C_{25}$ alkyl, $^-OC(O)C_{10}$-$C_{25}$ alkenyl, or $^-OC(O)C_{10}$-$C_{25}$ alkynyl. In some embodiments, each hydrogen atom in $C_{10}$-$C_{25}$ alkyl, $C_{10}$-$C_{25}$ alkenyl, or $C_{10}$-$C_{25}$ alkynyl is independently optionally substituted with halo, hydroxy, amino, oxo, or $OR^{10}$. In some embodiments, $R^{10}$ is independently H, $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, —C(O)$C_1$-$C_6$ alkyl, —C(O)$C_1$-$C_6$ alkenyl, —C(O)$C_1$-$C_6$ alkynyl, —C(O)$C_{10}$-$C_{25}$ alkyl, —C(O)$C_{10}$-$C_{25}$ alkenyl, —C(O)$C_{10}$-$C_{25}$ alkynyl, and wherein each hydrogen atom in $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, —C(O)$C_1$-$C_6$ alkyl, —C(O)$C_1$-$C_6$ alkenyl, —C(O)$C_1$-$C_6$ alkynyl, —C(O)$C_{10}$-$C_{25}$ alkyl, —C(O)$C_{10}$-$C_{25}$ alkenyl, —C(O)$C_{10}$-$C_{25}$ alkynyl is independently optionally substituted with halo, hydroxy, or amino. In some embodiments, the divalent cation is magnesium, calcium, or iron. In some embodiments, the salt of formula II comprises a stearate. In some embodiments, the salt of formula II is calcium stearate.

In some embodiments, $M^1$ is a monovalent cation and is associated with only one of $R^8$ or $R^9$. In some embodiments, the formulation comprises a stearate. In some embodiments, the formulation comprises sodium stearate.

The formulation for a lubricant may comprise a certain percentage of the salt of formula II. The percentage of the salt of formula II for the formulation for a lubricant may be at least about 2%, at least about 3%, at least about 4%, or at least about 5% by weight of the formulation. In some embodiments, the salt of formula II for the formulation for a lubricant may be less than about 20%, less than about 15%, or less than about 10% by weight of the formulation. In some embodiments, the salt of formula II is about 2%, about 3%, about 4%, about 5%, about 6%, about 7%, about 8%, about 9%, about 10%, about 12%, about 15%, or about 20% by weight of the formulation. In some embodiments, the salt of formula II is about 2% to about 20%, about 2% to about 15%, about 3% to about 15%, about 3% to about 10%, or about 5% to about 10% by weight of the formulation.

In some embodiments, the formulation comprises a component that modifies the thickness of the formulation, the texture of the formulation, or both, while maintaining heat tolerance. In some embodiments, the formulation for a lubricant comprises a compound of formula V

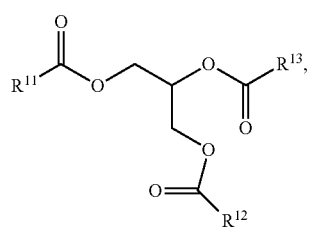

(V)

or a salt thereof. In some embodiments, each of $R^{11}$, $R^{12}$, and $R^{13}$ is independently $C_{10}$-$C_{25}$ alkyl, $C_{10}$-$C_{25}$ alkenyl, or $C_{10}$-$C_{25}$ alkynyl. In some embodiments, each hydrogen atom in $C_{10}$-$C_{25}$ alkyl, $C_{10}$-$C_{25}$ alkenyl, or $C_{10}$-$C_{25}$ alkynyl is independently optionally substituted with halo, hydroxy, amino, oxo, or $OR^{14}$. In some embodiments, $R^{14}$ is H, $C_1$-$C_6$ alkyl, $C_1$-$C_6$ alkenyl, or $C_1$-$C_6$ alkynyl, and wherein each hydrogen atom in $C_1$-$C_6$ alkyl, $C_1$-$C_6$ alkenyl, and $C_1$-$C_6$ alkynyl is independently optionally substituted with a halo, hydroxy, or an amino. In some embodiments, each of $R^{11}$, $R^{12}$, and $R^{13}$ is independently $C_{10}$-$C_{25}$ alkyl or $C_{10}$-$C_{25}$ alkenyl. In some embodiments, each of $R^{11}$, $R^{12}$, and $R^{13}$ is independently $C_{10}$-$C_{25}$ alkyl. In some embodiments, the compound of formula V comprises a stearate. In some embodiments, the compound of formula V is glyceryl tristearate. In some embodiments, the compound of formula V is found in the base oil.

In some embodiments, the formulation for a lubricant comprises a saturated fatty acid. In some embodiments, the formulation for a lubricant comprises a myristic acid.

In some embodiments, the formulation comprises a long chain alcohol. Illustratively, the alcohol may be a primary alcohol or a secondary alcohol. Illustratively, the alcohol may be saturated or unsaturated. In some embodiments, the formulation comprises an alcohol of the formula $HO(CH_2)_d CH_3$, where d is an integer from 7 to 12. In some embodiments, the alcohol is stearyl alcohol. In some embodiments, the alcohol is cetyl alcohol.

The formulation for a lubricant may comprise a certain percentage of the compound of formula V, a long chain alcohol, a saturated fatty acid, or salts thereof. The percentage of compound of formula V, a long chain alcohol, a saturated fatty acid, or salts thereof for the formulation for a lubricant may be at least about 2%, at least about 3%, at least about 4%, or at least about 5% by weight of the formulation. In some embodiments, the compound of formula V, a long chain alcohol, a saturated fatty acid, or salts thereof for the formulation for a lubricant may be less than about 20%, less than about 15%, or less than about 10% by weight of the formulation. In some embodiments, the compound of formula V, a long chain alcohol, a saturated fatty acid, or salts thereof is about 2%, about 3%, about 4%, about 5%, about 6%, about 7%, about 8%, about 9%, about 10%, about 12%, about 15%, or about 20% by weight of the formulation. In some embodiments, the compound of formula V, a long chain alcohol, a saturated fatty acid, or salts thereof is about 2% to about 20%, about 2% to about 15%, about 3% to about 15%, about 3% to about 10%, or about 5% to about 10% by weight of the formulation.

In some embodiments, the formulation for the lubricant comprises a fragrance. In some embodiments, the fragrance comprises an essential oil. In some embodiments, the essential oil is mace essential oil.

The formulation may comprise a certain percentage by weight of the fragrance. In some embodiments, the fragrance is at least about 1%, at least about 3%, at least about 5%, or at least about 10% by weight of the formulation. In some embodiments, the fragrance is up to about 25%, up to about 20%, or up to about 15% by weight of the formulation. The fragrance may be about 2%, about 3%, about 4%, about 5%, about 6%, about 7%, about 7.5%, about 8%, about 9%, about 10%, about 12%, about 15%, about 20%, or about 25% by weight of the formulation. The fragrance may be about 2% to about 25%, about 2% to about 20%, about 2% to about 15%, about 3% to about 12%, or about 5% to about 12% by weight of the formulation.

In some embodiments, the formulation for the lubricant comprises at least one anti-oxidant. The anti-oxidant may provide protection for the fatty components against heat-degradation. In addition, the anti-oxidant may act as a preservative and may assist the body's healing processes. In some embodiments, the at least one anti-oxidant comprises a tocopherol or a lipoic acid. In some embodiments, the anti-oxidant comprises a blend of tocopherols. In some embodiments, the lipoic acid is an alpha-lipoic acid.

The formulation may comprise a certain percentage by weight of the at least one anti-oxidant. In some embodiments, the at least one anti-oxidant is at least about 1% or at least about 3% by weight of the formulation. In some embodiments, the at least one anti-oxidant is up to about 20%, up to about 15%, or up to about 10% by weight of the formulation. The at least one anti-oxidant may be about 1%, about 2%, about 3%, about 4%, about 5%, about 6%, about 7%, about 7.5%, about 8%, about 9%, about 10%, about 12%, about 15%, or about 20% by weight of the formulation. The at least one anti-oxidant may be about 1% to about 20%, about 1% to about 15%, about 1% to about 10%, or about 2% to about 8% by weight of the formulation.

In some embodiments, the formulation for the lubricant comprises at least one anti-inflammatory. In some embodiments, the at least one anti-inflammatory comprises a caryophyllene or a phyto-aromatic. In some embodiments, the phyto-aromatic comprises a terpene.

The formulation may comprise a certain percentage by weight of the at least one anti-inflammatory. In some embodiments, the at least one anti-inflammatory is at least about 1% or at least 2% by weight of the formulation. In some embodiments, the at least one anti-inflammatory is up to about 20%, up to about 15%, or up to about 10% by weight of the formulation. The at least one anti-inflammatory may be about 1%, about 2%, about 3%, about 4%, about 5%, about 6%, about 7%, about 7.5%, about 8%, about 9%, about 10%, about 12%, about 15%, or about 20% by weight of the formulation. The at least one anti-inflammatory may be about 1% to about 20%, about 1% to about 15%, about 1% to about 10%, or about 2% to about 8% by weight of the formulation.

In some embodiments, the formulation may comprise a scented component. In some embodiments, the scented component is a fragrance oil. In some embodiments, the scented component is biocompatible. In some embodiments, the scented component is selected from the group consisting of hexyl acetate, fructone, ethyl methylphenylglycidate, and combinations thereof. In some embodiments, the scented component is hexyl acetate. In some embodiments, the scented component is fructone. In some embodiments, the scented component is ethyl methylphenylglycidate. In some embodiments, the scented component comprises a lactone. Additional disclosure related to scented components can be found in U.S. patent application Ser. No. 15/240,538, which is herein expressly incorporated by reference in its entirety.

Another aspect of the present disclosure is a method of preparing a formulation for a lubricant. Illustratively, the method may comprise heating a base oil, mixing the base oil with a compound of formula V, and mixing the base oil with a phospholipid.

In some embodiments, the step of heating comprises heating the base oil to a temperature of about 80° F. to about 350° F., about 80° F. to about 325° F., about 90° F. to about 325° F., about 90° F. to about 275° F., or about 120° F. to about 225° F.

In some embodiments, the step of mixing is performed by stirring at a rate of about 25 to about 1,000 RPMs, about 75 to about 1,000 RPMs, about 75 to about 800 RPMs, about 100 to about 800 RPMs, about 100 to about 700 RPMs, or about 100 to about 600 RPMs. In some embodiments, the step of mixing the base oil with the compound of formula V occurs before the step of mixing the base oil with the phospholipid.

In some embodiments, the method comprises mixing at least one antioxidant, at least one anti-inflammatory, or a mixture of both with the base oil. In some embodiments, the step of mixing produces a suspension.

In some embodiments, the method further comprises de-gassing the suspension. Illustratively, the step of de-gassing may be performed by applying a vacuum to the suspension.

In some illustrative embodiments, the method further comprises a cooling the suspension to a temperature of about 100° F. to about 150° F. In some embodiments, the suspension is de-gassed prior to cooling.

In some embodiments, the method comprising mixing the cooled suspension with a fragrance, at least one anti-oxidant, at least one anti-inflammatory, or a mixture thereof.

Figure 2A:
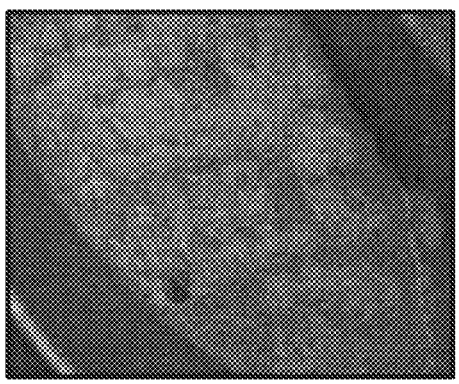
FIGS. 2A-2F show images from an experiment using a lubricant in accordance with the present disclosure with an electrocautery probe.
Figure 2B:
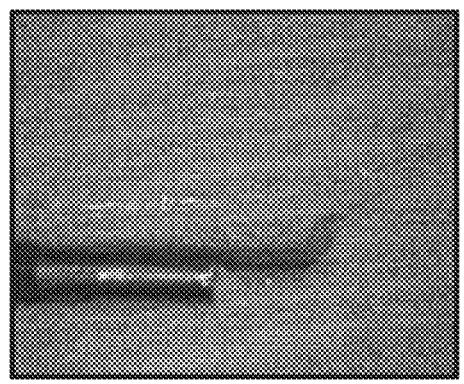
Figure 2C:
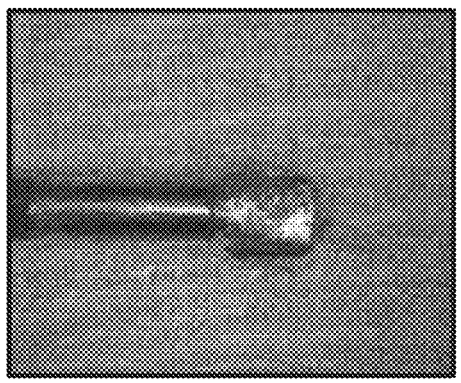
Figure 2D:
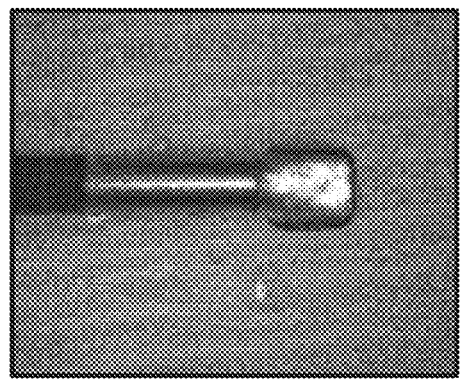

Illustratively, stearic acid is a fully saturated fat and esterified stearic acid may be a primary component of avocado oil. Adding glyceryl tristearate to a base oil comprising stearic acid may modify the thickness of the oil and calibrate it to a desired texture while retaining the high-heat tolerance. These properties may allow for greater self-healing. In some illustrative embodiments, the formulation comprises hydrogenated phosphatidylcholine. In some embodiments, the formulation comprises d-alpha tocopherol oil, which may provide protection for the fatty components against heat-degradation. This protection may be due to its potent anti-oxidant properties, which may also allow it to act as a preservative and may assist the body's healing processes. In some illustrative embodiments, these four components may comprise a first-phase of the non-stick mechanism. Illustratively, these components may provide improved thermal stability and survive a greater number of burns before degradation compared to a comparative lubricant. A possible benefit to an exemplary formulation may be a change in viscosity upon heating. A comparative lubricant remained relatively viscous even upon heating, which restricted its self-healing capacity on the probe. A formulation in accordance with the present disclosure readily flowed on the surface of the probe when heated, which may allow bare-spots to recover quickly. This is also marked by the observation of a large amount of comparative lubricant remaining on the probe even though it has been depleted on the working-side of the probe (see FIG. 2C). A lubricant in accordance with the present disclosure may become largely depleted off the probe, but thanks to the second-phase mechanism, it may continue to retain non-stick properties.

Figure 2E:
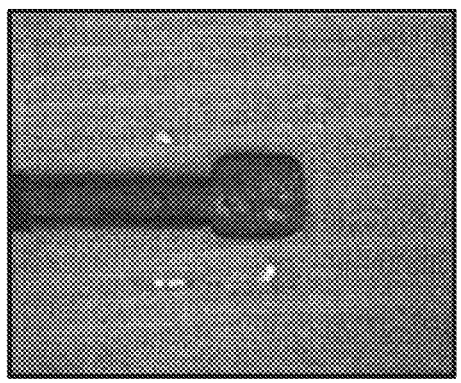

In some embodiments, the formulation may provide a second nonstick phase that may prolong the performance of the formulation and may be unrelated to the hydrophobic/hydrophilic nature of lecithin. The second phase may instead rely on the properties of a salt (e.g. calcium stearate) as an anti-caking, a mold-release agent, and a water-repelling agent. As a salt, this molecule may be able to tolerate immense amounts of heat before degrading and may be used throughout the food and pharmaceutical industry for mold-release and anti-caking applications. In some formulations in accordance with the present disclosure, the calcium stearate may be suspended in the solution and may become deposited onto the probe. As the fatty components of the formulation may be lost to heat, the calcium stearate may form a protective barrier on the probe, which may provide a non-stick surface that may be highly resilient against heat. Furthermore, the mix of fatty components in the new formulation may have less propensity to accumulate char, and so may be less susceptible to decreased performance after several cautery applications in comparison to a comparative lubricant. Instead, a relatively thin layer of residue is left behind which may minimally impede the transfer of energy from the probe to the tissue. Because the salt (e.g. calcium stearate) may be effective at preventing sticking, little additional residue accumulates with continued usage. Additionally, the amount of tissue adhering to the probe with some formulations in accordance with the present disclosure tended to be much smaller than what was typical of the original formulation (see FIGS. 2B and 2E).

In some embodiments, the formulation comprises a fragrance, such as a fragrance oil. In some embodiments, the fragrance oil is mace oil and is derived from the aril of the nutmeg (*M. fragrans*). Illustratively, mace oil may be preferred due to its availability, lack of known-allergens, low sensitization potential, strong-but-pleasing odor, and the high boiling point, which may allow it to persist for a long period before it, is depleted. Additionally, mace oil is of relatively low volatility compared to many other plant essential oils, which will facilitate the manufacturing process and minimize evaporative loss of oil due to the necessary heating of the product for bottling.

In some embodiments, the formulation for a lubricant comprises a phospholipid such as a fully hydrogenated phosphatidylcholine. In some illustrative embodiments, the phospholipid may be dissolved in a mix of saturated fats with high boiling points. In some embodiments, the base oil comprises avocado oil and the formulation comprises of glyceryl tristearate, which are both known for their unusually high smoke points and boiling points, respectively. Illustratively, using fully hydrogenated compounds may provide greater heat-stability.

While the disclosure has been illustrated and described in detail in the foregoing drawings and description, the same is to be considered as exemplary and not restrictive in character, it being understood that only illustrative embodiments thereof have been shown and described and that all changes and modifications that come within the spirit of the disclosure are desired to be protected.

EXAMPLES

Example 1

Lubricant Formulation

A formulation for a lubricant included a base oil, a tristearate, a stearate salt, a phospholipid, an anti-oxidant, a fragrance, and an anti-inflammatory. The base oil was avocado oil, the tristearate was glyceryl tristearate, the stearate salt was calcium stearate, the phospholipid was hydrogenated phosphatidyl choline, the anti-oxidant was mixed tocopherol oil, the fragrance was mace essential oil, and the anti-inflammatory was beta-caryophyllene. The components were combined in the amounts described below via blending to prepare the lubricant.

| | |
|---|---|
| 70% | Avocado oil |
| 6% | Glyceryl Tristearate |
| 6% | Calcium Stearate |
| 5% | Hydrogenated Phosphatidylcholine |

-continued

| | |
|---|---|
| 3% | mixed tocopherol oil |
| 7.5% | Mace Essential oil |
| 2.5% | beta-Caryophyllene |

The resulting lubricant was generally a liquid at room temperature and generally colorless.

Example 2

Process for Mixing the Lubricant

The base oil (e.g. avocado) is added to a container under stirring of ~120-500 RPMs and brought to a temperature of ~150° F.-180° F. Secondly, with continued heating and stirring, the oil-soluble compounds are added in no specific order, including glyceryl tristearate and the tocopherols. Stirring and heating are continued until the components are generally dissolved. Next, calcium stearate and hydrogenated phosphatidylcholine are added to create a suspension and stirring is continued. The heat is reduced to allow the mixture to slowly cool while stirring is continued. At this stage, a de-gassing vacuum-procedure may be conducted in order to remove small air-bubbles that may have become entrapped during the stirring and additions.

Once the mixture has cooled to about 110° F. to about 120° F., the caryophyllenes and mace oil are added. Heat is removed, but stirring continues until the mixture has fallen to about 90° F., whereupon stirring can cease and the mixture is allowed to set into its final cream-lie consistency.

Example 3

Process for Coating a Probe with a Lubricant

Application to the electrocautery tips consists of a simple dipping of the probe into a reservoir of a formulation according to Example 1 or 2, followed by a gentle shaking or tapping of the probe to loosen any excess. Wiping will also be possible, as in the case of the current Electro-Lube formulation.

Example 4

Lubricant Performance

Figure 2F:
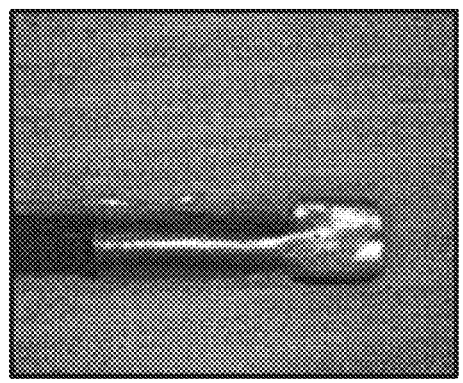

The following experimental conditions were devised to compare the performance of a comparative lubricant formulation against the formulation prepared in Example 1 accordance with the present disclosure. A stainless-steel spatula probe was evenly coated in either a comparative lubricant (Electro-Lube®) or the lubricant of Example 1 (see FIG. 2F) and was subjected to repeated coagulation electrocautery at full power against the "skin-side" of a fresh chicken breast. The probe was positioned against the surface of the chicken in a manner that generated continuous arcing between the probe and flesh, and lasted about 5-10 seconds each. After each burn, the probe was moved to an adjacent un-affected area and repeated (see FIG. 2A). This continued until flesh adhered to the probe, at which point the trial was considered complete. The number of burns achieved was recorded, and the probe was photographed for documentation. The probe was then cleaned using a wire-wheel and wiped. The same probe was used for all trials. Eleven trials were conducted each for the original and revised formula.

Data was analyzed with a Welch's t-test using the statistics program R, see FIG. 1. The number of burns per application was greater when using the lubricant of Example 1 (M=17.73, SD=5.59) than the comparative lubricant (M=7.55, SD=2.70). This difference is statistically significant (t(14.42)=−5.44, p<0.001), confirming that the lubricant of Example 1 confers on average an additional 10 electrocautery burns per application.

Example 5

Lubricant Formulation

The lubricant for this example was Electrolube® available from Mectra Labs.

Example 6

Lubricant Formulation

A formulation for a lubricant the following components. The components were combined as described above in the amounts described below to prepare the lubricant.

| | |
|---|---|
| 9 g | Food Grade Liquid Lecithin |
| 0.5 g | Glyceryl Tristearate |
| 0.5 g | Mace essential oil |

Example 7

Lubricant Formulation

A formulation for a lubricant included the following components. The components were combined as described above in the amounts described below to prepare the lubricant.

| | |
|---|---|
| 9 g | Heat-Resistant Lecithin |
| 0.5 g | Glyceryl Tristearate |
| 0.5 g | Mace essential oil |

Example 8

Lubricant Formulation

A formulation for a lubricant included the following components. The components were combined as described above in the amounts described below to prepare the lubricant.

| | |
|---|---|
| 9.3 g | Phosal Lecithin |
| 0.2 g | Glyceryl Tristearate |
| 0.5 g | Mace essential oil |

Example 9

Lubricant Formulation

A formulation for a lubricant included the following components. The components were combined as described above in the amounts described below to prepare the lubricant.

| | |
|---|---|
| 8 g | Avocado oil |
| 0.2 g | Tocopherols |
| 0.5 g | Trimyristin |
| 0.5 g | Hydrogenated phosphatidyl choline |
| 0.5 g | Calcium stearate |

Example 10

Lubricant Formulation

A formulation for a lubricant included the following components. The components were combined as described above in the amounts described below to prepare the lubricant.

| | |
|---|---|
| 8 g | Avocado oil |
| 0.2 g | Tocopherols |
| 0.5 g | Stearin |
| 0.5 g | Hydrogenated phosphatidyl choline |
| 0.5 g | Calcium stearate |

Example 11

Lubricant Formulation

A formulation for a lubricant included the following components. The components were combined as described above in the amounts described below to prepare the lubricant.

| | |
|---|---|
| 8 g | Avocado oil |
| 0.2 g | Tocopherols |
| 0.35 g | Trimyristin |
| 0.5 g | Stearin |
| 0.5 g | Hydrogenated phosphatidyl choline |
| 0.5 g | Calcium stearate |

Example 12

Lubricant Formulation

A formulation for a lubricant included the following components. The components were combined as described above in the amounts described below to prepare the lubricant.

| | |
|---|---|
| 8 g | Avocado oil |
| 0.2 g | Tocopherols |
| 0.5 g | Cetyl alcohol |
| 0.5 g | Hydrogenated phosphatidyl choline |
| 0.5 g | Calcium stearate |

Example 13

Lubricant Formulation

A formulation for a lubricant included the following components. The components were combined as described above in the amounts described below to prepare the lubricant.

| | |
|---|---|
| 8 g | Avocado oil |
| 0.2 g | Tocopherols |
| 0.5 g | Stearyl alcohol |
| 0.5 g | Hydrogenated phosphatidyl choline |
| 0.5 g | Calcium stearate |

Example 14

Lubricant Formulation

A formulation for a lubricant included the following components. The components were combined as described above in the amounts described below to prepare the lubricant.

| | |
|---|---|
| 8 g | Avocado oil |
| 0.2 g | Tocopherols |
| 0.5 g | Stearic acid |
| 0.5 g | Hydrogenated phosphatidyl choline |
| 0.5 g | Calcium stearate |

Example 15

Lubricant Formulation

A formulation for a lubricant included the following components. The components were combined as described above in the amounts described below to prepare the lubricant.

| | |
|---|---|
| 8 g | Avocado oil |
| 0.2 g | Tocopherols |
| 0.5 g | Stearic acid |
| 0.5 g | Myristic acid |
| 0.5 g | Hydrogenated phosphatidyl choline |
| 0.5 g | Calcium stearate |

Example 16

Lubricant Formulation

A formulation for a lubricant included the following components. The components were combined as described above in the amounts described below to prepare the lubricant.

| | |
|---|---|
| 7.75 g | Triolein |
| 0.75 g | Stearin |
| 1.5 g | alpha tocopherol |

Example 17

Lubricant Formulation

A formulation for a lubricant included the following components. The components were combined as described above in the amounts described below to prepare the lubricant.

| | |
|---|---|
| 80% | Grapeseed oil |
| 8% | Glyceryl Tristearate |
| 5% | Calcium Stearate |
| 5% | Hydrogenated Phosphatidylcholine |
| 2% | mixed tocopherol oil |

Example 18

Lubricant Formulation

A formulation for a lubricant included the following components. The components were combined as described above in the amounts described below to prepare the lubricant.

| | |
|---|---|
| 8 g | Triolein |
| 0.2 g | Tocopherols |
| 0.5 g | Stearin |
| 0.5 g | Hydrogenated phosphatidyl choline |
| 0.5 g | Calcium stearate |

Example 19

Lubricant Performance

The lubricants described in Examples 5-18 were tested as described in Example 4. The results are shown in FIG. 1.

Example 20

Lubricant Formulation

A formulation for a lubricant included a base oil, a tristearate, and a fragrance. The components were combined in the amounts described below via blending to prepare the lubricant.

| | |
|---|---|
| 87.5% | Food Grade Liquid Lecithin |
| 2.5% | Stearin |
| 10% | Fragrance oil |

The liquid lecithin was heated to about 150° F. and the stearin is added. The mixture is then stirred at temp until the stearin has fully dissolved. Then the temp is lowered to about 110° F.-about 120° F. where the fragrance oil is added before letting cool to room temp.

ADDITIONAL EMBODIMENTS

The following exemplary embodiments are provided, the numbering of which is not to be construed as designating levels of importance:

Embodiment 1 provides a formulation for a lubricant comprising
a base oil comprising a compound of the formula I

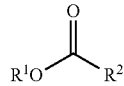

(I)

wherein $R^1$ is H, $C_1$-$C_6$ alkyl, $C_1$-$C_6$ alkenyl, or $C_1$-$C_6$ alkynyl, wherein each hydrogen atom in $C_1$-$C_6$ alkyl, $C_1$-$C_6$ alkenyl, or $C_1$-$C_6$ alkynyl is independently optionally substituted with halo, hydroxy, amino, oxo, or $OR^3$; $R^2$ is $C_{10}$-$C_{25}$ alkyl, $C_{10}$-$C_{25}$ alkenyl, or $C_{10}$-$C_{25}$ alkynyl, and wherein each hydrogen atom in $C_{10}$-$C_{25}$ alkyl, $C_{10}$-$C_{25}$ alkenyl, or $C_{10}$-$C_{25}$ alkynyl is independently optionally substituted with halo, hydroxy, amino, oxo, or $OR^7$; or a salt thereof;
a phospholipid; or a salt thereof; and
a salt of the formula

 (II)

wherein $M^1$ is a divalent cation, $R^7$ and $R^8$ are independently $^-OC(O)C_{10}$-$C_{25}$ alkyl, $^-OC(O)C_{10}$-$C_{25}$ alkenyl, or $^-OC(O)C_{10}$-$C_{25}$ alkynyl, and wherein each hydrogen atom in $C_{10}$-$C_{25}$ alkyl, $C_{10}$-$C_{25}$ alkenyl, or $C_{10}$-$C_{25}$ alkynyl is independently optionally substituted with halo, hydroxy, amino, oxo, or $OR^{10}$, wherein each of $R^3$, $R^7$, and $R^{10}$ is independently H, $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, —C(O)$C_1$-$C_6$ alkyl, —C(O)$C_1$-$C_6$ alkenyl, —C(O)$C_1$-$C_6$ alkynyl, —C(O)$C_{10}$-$C_{25}$ alkyl, —C(O)$C_{10}$-$C_{25}$ alkenyl, —C(O)$C_{10}$-$C_{25}$ alkynyl, wherein each hydrogen atom in $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, —C(O)$C_1$-$C_6$ alkyl, —C(O)$C_1$-$C_6$ alkenyl, —C(O)$C_1$-$C_6$ alkynyl, —C(O)$C_{10}$-$C_{25}$ alkyl, —C(O)$C_{10}$-$C_{25}$ alkenyl, —C(O)$C_{10}$-$C_{25}$ alkynyl is independently optionally substituted with halo, hydroxy, or amino.

Embodiment 2 provides the formulation of Embodiment 1, wherein $R^1$ is H; or a salt thereof.

Embodiment 3 provides the formulation of Embodiment 1 or 2, wherein $R^1$ is $C_1$-$C_6$ alkyl, and wherein each hydrogen atom in $C_1$-$C_6$ alkyl is independently optionally substituted with halo, hydroxy, amino, oxo, or $OR^3$; or a salt thereof.

Embodiment 4 provides the formulation of any of the preceding Embodiments, wherein $R^1$ is $C_1$-$C_6$ alkyl and wherein each hydrogen atom in $C_1$-$C_6$ alkyl is independently optionally substituted with $OR^3$, wherein each $R^3$ is independently H, $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, —C(O)$C_1$-$C_6$ alkyl, —C(O)$C_1$-$C_6$ alkenyl, —C(O)$C_1$-$C_6$ alkynyl, —C(O)$C_{10}$-$C_{25}$ alkyl, —C(O)$C_{10}$-$C_{25}$ alkenyl, or —C(O)$C_{10}$-$C_{25}$ alkynyl, wherein each hydrogen atom in $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, —C(O)$C_1$-$C_6$ alkyl, —C(O)$C_1$-$C_6$ alkenyl, —C(O)$C_1$-$C_6$ alkynyl, —C(O)$C_{10}$-$C_{25}$ alkyl, —C(O)$C_{10}$-$C_{25}$ alkenyl, and —C(O)$C_{10}$-$C_{25}$ alkynyl is independently optionally substituted with halo, hydroxy, or amino; or a salt thereof.

Embodiment 5 provides the formulation of any of the preceding Embodiments, wherein each $R^3$ is independently —C(O)$C_1$-$C_6$ alkyl, —C(O)$C_1$-$C_6$ alkenyl, —C(O)$C_1$-$C_6$ alkynyl, —C(O)$C_{10}$-$C_{25}$ alkyl, —C(O)$C_{10}$-$C_{25}$ alkenyl, —C(O)$C_{10}$-$C_{25}$ alkynyl, wherein each hydrogen atom in —C(O)$C_1$-$C_6$ alkyl, —C(O)$C_1$-$C_6$ alkenyl, —C(O)$C_1$-$C_6$ alkynyl, —C(O)$C_{10}$-$C_{25}$ alkyl, —C(O)$C_{10}$-$C_{25}$ alkenyl, and —C(O)$C_{10}$-$C_{25}$ alkynyl is independently optionally substituted with halo, hydroxy, or amino; or a salt thereof.

Embodiment 6 provides the formulation of any of the preceding Embodiments, wherein each $R^3$ is independently —C(O)$C_{10}$-$C_{25}$ alkyl, —C(O)$C_{10}$-$C_{25}$ alkenyl, —C(O)$C_{10}$-$C_{25}$ alkynyl, wherein each hydrogen atom in —C(O)$C_{10}$-$C_{25}$ alkyl, —C(O)$C_{10}$-$C_{25}$ alkenyl, and —C(O)$C_{10}$-$C_{25}$ alkynyl is independently optionally substituted with halo, hydroxy, or amino.

Embodiment 7 provides the formulation of Embodiment 1, wherein R 1 is of the formula III

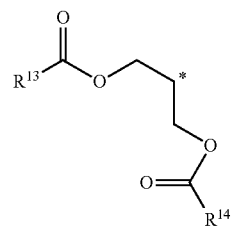

(III)

wherein each of $R^{14}$ and $R^{15}$ is independently $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, or $C_{10}$-$C_{25}$ alkynyl, wherein each hydrogen atom in $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, and $C_{10}$-$C_{25}$ alkynyl is independently optionally substituted with halo, hydroxy, or amino; and

* denotes a point of attachment; or a salt thereof.

Embodiment 8 provides the formulation of any of the preceding Embodiments, wherein each of $R^{14}$ and $R^{15}$ is $C_{10}$-$C_{25}$ alkyl, $C_{10}$-$C_{25}$ alkenyl, or $C_{10}$-$C_{25}$ alkynyl, and wherein each hydrogen atom in $C_{10}$-$C_{25}$ alkyl, $C_{10}$-$C_{25}$ alkenyl, and $C_{10}$-$C_{25}$ alkynyl is independently optionally substituted with halo, hydroxy, or amino; or a salt thereof.

Embodiment 9 provides the formulation of any of the preceding Embodiments, wherein each of $R^{14}$ and $R^{15}$ is $C_{10}$-$C_{25}$ alkenyl or $C_{10}$-$C_{25}$ alkynyl, and wherein each hydrogen atom in $C_{10}$-$C_{25}$ alkenyl and $C_{10}$-$C_{25}$ alkynyl is independently optionally substituted with halo, hydroxy, or amino; or a salt thereof.

Embodiment 10 provides the formulation of any of the preceding Embodiments, wherein $R^7$ is independently H, $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, and wherein each hydrogen atom in $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, and $C_{10}$-$C_{25}$ alkynyl is independently optionally substituted with halo, hydroxy, or amino; or a salt thereof.

Embodiment 11 provides the formulation of any of the preceding Embodiments, wherein $R^7$ is independently H, $C_1$-$C_6$ alkyl, $C_1$-$C_6$ alkenyl, $C_1$-$C_6$ alkynyl, wherein each hydrogen atom in $C_1$-$C_6$ alkyl, $C_1$-$C_6$ alkenyl, and $C_1$-$C_6$ alkynyl is independently optionally substituted with halo, hydroxy, or amino; or a salt thereof.

Embodiment 12 provides the formulation of any of the preceding Embodiments, wherein $R^2$ is $C_{10}$-$C_{25}$ alkyl, $C_{10}$-$C_{25}$ alkenyl, or $C_{10}$-$C_{25}$ alkynyl, and wherein each hydrogen atom in $C_{10}$-$C_{25}$ alkyl, $C_{10}$-$C_{25}$ alkenyl, and $C_{10}$-$C_{25}$ alkynyl is independently optionally substituted with halo, hydroxy, amino, or oxo; or a salt thereof.

Embodiment 13 provides the formulation any of the preceding Embodiments, wherein $R^2$ is $C_{10}$-$C_{25}$ alkyl or $C_{10}$-$C_{25}$ alkenyl, and wherein each hydrogen atom in $C_{10}$-$C_{25}$ alkyl and $C_{10}$-$C_{25}$ alkenyl is independently optionally substituted with halo, hydroxy, amino, or oxo.

Embodiment 14 provides the lubricant of any of the preceding Embodiments, wherein $R^3$ is H, $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, or $C_{10}$-$C_{25}$ alkynyl, wherein each hydrogen atom in $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, and $C_{10}$-$C_{25}$ alkynyl, is independently optionally substituted with halo, hydroxy, or amino.

Embodiment 15 provides the formulation of any of the preceding Embodiments, wherein $R^{10}$ is H, $C_1$-$C_6$ alkyl, $C_1$-$C_6$ alkenyl, or $C_1$-$C_6$ alkynyl, and wherein each hydrogen atom in $C_1$-$C_6$ alkyl, $C_1$-$C_6$ alkenyl, and $C_1$-$C_6$ alkynyl is independently optionally substituted with a halo, hydroxy, or an amino.

Embodiment 16 provides the formulation of any of the preceding Embodiments, wherein the base oil has a smoke point of at least 450° F., at least 475° F., at least 490° F., at least 500° F., or at least 510° F.

Embodiment 17 provides the formulation of any of the preceding Embodiments, wherein at least the base oil is at least 40% by weight of the formulation.

Embodiment 18 provides the formulation of any of the preceding Embodiments, wherein the base oil is at least 50% by weight of the formulation.

Embodiment 19 provides the formulation of any of the preceding Embodiments, wherein the base oil is at least 60% by weight of the formulation.

Embodiment 20 provides the formulation of any of the preceding Embodiments, wherein the base oil is at least 65% by weight of the formulation.

Embodiment 21 provides the formulation of any of the preceding Embodiments, wherein compound of formula I is at least 20% by weight of the base oil.

Embodiment 22 provides the formulation of any of the preceding Embodiments, wherein compound of formula I is at least 30% by weight of the base oil.

Embodiment 23 provides the formulation of any of the preceding Embodiments, wherein compound of formula I is at least 40% by weight of the base oil.

Embodiment 24 provides the formulation of any of the preceding Embodiments, wherein compound of formula I is at least 50% by weight of the base oil.

Embodiment 25 provides the formulation of any of the preceding Embodiments, wherein the phospholipid has a structure according to formula II

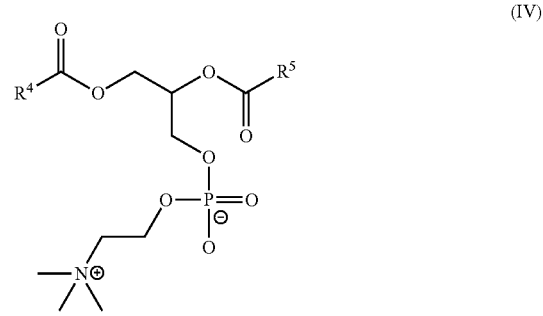

(IV)

wherein each of $R^4$ and $R^5$ is independently $C_{10}$-$C_{25}$ alkyl, $C_{10}$-$C_{25}$ alkenyl, or $C_{10}$-$C_{25}$ alkynyl, and wherein each hydrogen atom in $C_{10}$-$C_{25}$ alkyl, $C_{10}$-$C_{25}$ alkenyl, and $C_{10}$-$C_{25}$ alkynyl is independently optionally substituted with halo, hydroxy, amino, oxo, or $OR^6$;

wherein $R^6$ is H, $C_1$-$C_6$ alkyl, $C_1$-$C_6$ alkenyl, or $C_1$-$C_6$ alkynyl, and wherein each hydrogen atom in $C_1$-$C_6$ alkyl, $C_1$-$C_6$ alkenyl, and $C_1$-$C_6$ alkynyl is independently optionally substituted with halo, hydroxy, or amino, or a salt thereof.

Embodiment 26 provides the formulation of Embodiment 25, wherein each of $R^4$ and $R^5$ is independently $C_{10}$-$C_{25}$ alkyl.

Embodiment 27 provides the formulation of Embodiment 25 or 26, wherein the phospholipid or salt thereof is a phosphatidyl choline.

Embodiment 28 provides the formulation of any one of Embodiments 25-27, wherein the phospholipid or a salt thereof comprises at least one $C_{10}$-$C_{25}$ alkyl.

Embodiment 29 provides the formulation of any one of Embodiments 25-28, wherein the phospholipid or a salt thereof is substantially free from a $C_{10}$-$C_{25}$ alkenyl.

Embodiment 30 provides the formulation of any one of Embodiments 25-29, wherein the phospholipid or a salt thereof is at least 2% by weight of the formulation.

Embodiment 31 provides the formulation of any one of Embodiments 25-30, wherein the phospholipid or a salt thereof is at least 3% by weight of the formulation.

Embodiment 32 provides the formulation of any one of Embodiments 25-31, wherein the phospholipid or a salt thereof is less than 15% by weight of the formulation.

Embodiment 33 provides the formulation of any one of Embodiments 25-32, wherein the phospholipid or a salt thereof is less than 10% by weight of the formulation.

Embodiment 34 provides the formulation of any one of Embodiments 25-33, wherein the salt of formula II is at least 2% by weight of the formulation.

Embodiment 35 provides the formulation of any one of Embodiments 25-34, wherein the salt of formula II is at least 3% by weight of the formulation.

Embodiment 36 provides the formulation of any one of Embodiments 25-35, wherein the salt of formula II is less than 15% by weight of the formulation.

Embodiment 37 provides the formulation of any of the any one of Embodiments 25-36, wherein the salt of formula II is less than 10% by weight of the formulation.

Embodiment 38 provides the formulation of any one of Embodiments 25-37, wherein the salt of formula II is calcium stearate.

Embodiment 39 provides the formulation of any one of Embodiments 25-38, further comprising a compound of formula V

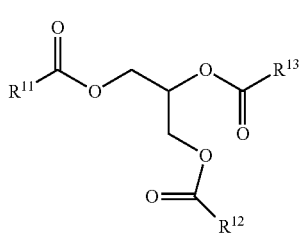

wherein each of $R^{11}$, $R^{12}$, and $R^{13}$ is independently $C_{10}$-$C_{25}$ alkyl, $C_{10}$-$C_{25}$ alkenyl, or $C_{10}$-$C_{25}$ alkynyl, and wherein each hydrogen atom in $C_{10}$-$C_{25}$ alkyl, $C_{10}$-$C_{25}$ alkenyl, or $C_{10}$-$C_{25}$ alkynyl is independently optionally substituted with halo, hydroxy, amino, oxo, or $OR^{14}$;

wherein $R^{14}$ is H, $C_1$-$C_6$ alkyl, $C_1$-$C_6$ alkenyl, or $C_1$-$C_6$ alkynyl, wherein each hydrogen atom in $C_1$-$C_6$ alkyl, $C_1$-$C_6$ alkenyl, and $C_1$-$C_6$ alkynyl is independently optionally substituted with a halo, hydroxy, or an amino, or a salt thereof.

Embodiment 40 provides the formulation of Embodiment 39, wherein each of $R^{11}$, $R^{12}$, and $R^3$ is independently $C_{10}$-$C_{25}$ alkyl or $C_{10}$-$C_{25}$ alkenyl.

Embodiment 41 provides the formulation of Embodiment 39, wherein each of $R^{11}$, $R^{12}$, and $R^{13}$ is independently $C_{10}$-$C_{25}$ alkyl.

Embodiment 42. Provides the formulation of any one of Embodiments 25-41, further comprising a fragrance.

Embodiment 43 provides the formulation of Embodiment 42, wherein the fragrance is up to about 15% by weight of the formulation.

Embodiment 44 provides the formulation of any one of Embodiments 25-43, further comprising at least one anti-oxidant.

Embodiment 45 provides the formulation of Embodiment 44, wherein the at least one anti-oxidant comprises a tocopherol.

Embodiment 46 provides the formulation of Embodiment 44, wherein the at least one anti-oxidant is up to about 10% by weight of the formulation.

Embodiment 47 provides the formulation of any one of Embodiments 25-46, further comprising at least one anti-inflammatory.

Embodiment 48 provides the formulation of Embodiment 47, wherein the at least one anti-inflammatory comprises a caryophyllene.

Embodiment 49 provides the formulation of Embodiment 47, wherein the at least one anti-oxidant is up to about 10% by weight of the formulation.

Embodiment 50 provides the formulation of any one of Embodiments 25-49, wherein the formulation is substantially free of a color.

Embodiment 51 provides a method of coating an electrocautery device with a formulation according to any of the preceding Embodiments, the method comprising
contacting a surface of an electrocautery device with the formulation according to any of the preceding Embodiments.

Embodiment 52 provides the method of Embodiment 51, wherein the step of contacting is performed by submerging a portion of the electrocautery device in a solution of the formulation.

Embodiment 53 provides a method of preparing the formulation according any of the preceding Embodiments, comprising
heating a base oil,
mixing the base oil with a compound of formula V, and
mixing the base oil with a phospholipid.

Embodiment 54 provides the method of Embodiment 53, wherein the step of heating comprising heating the base oil to a temperature of about 120° F. to about 225° F.

Embodiment 55 provides the method of Embodiment 53, wherein the step of mixing the base oil with the compound of formula V occurs before the step of mixing the base oil with the phospholipid.

Embodiment 56 provides the method of Embodiment 53, wherein the step of mixing is performed by stirring at a rate of about 100 to about 600 RPMs.

Embodiment 57 provides the method of Embodiment 53, wherein the method comprises mixing at least one anti-oxidant, at least one anti-inflammatory, or a mixture of both with the base oil to make a suspension.

Embodiment 58 provides the method of Embodiment 57, wherein the method further comprises degassing the suspension.

Embodiment 59 provides the method of Embodiment 58, wherein the step of de-gassing is performed by applying a vacuum.

Embodiment 60 provides the method of Embodiment 57, wherein the method further comprises a cooling the suspension to a temperature of about 100° F. to about 150° F.

Embodiment 61 provides the method of Embodiment 60, comprising mixing the cooled suspension with a fragrance, at least one anti-oxidant, at least one anti-inflammatory, or a mixture thereof.

Embodiment 62 provides a kit comprising
a formulation for a lubricant according to anyone of the preceding Embodiments, and
a cautery probe.

Embodiment 63 provides a method of cauterization comprising
applying a formulation for a lubricant according to any one of the preceding Embodiments to a cautery probe, and
cauterizing tissue with the cautery probe.

Embodiment 64 provides a formulation for a lubricant comprising
a base oil, and
a triglyceride.

Embodiment 65 provides the formulation of Embodiment 64, further comprising a scented component.

Embodiment 66 provides the formulation of Embodiment 64, wherein the base oil comprises a lecithin.

Embodiment 67 provides the formulation of Embodiment 64, wherein the triglyceride is saturated.

Embodiment 68 provides the formulation of Embodiment 67, wherein the triglyceride comprises a compound of formula V

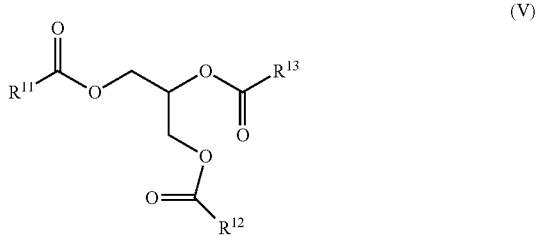

wherein each of $R^{11}$, $R^{12}$, and $R^{13}$ is independently $C_{10}$-$C_{25}$ alkyl, $C_{10}$-$C_{25}$ alkenyl, or $C_{10}$-$C_{25}$ alkynyl, and wherein each hydrogen atom in $C_{10}$-$C_{25}$ alkyl, $C_{10}$-$C_{25}$ alkenyl, or $C_{10}$-$C_{25}$ alkynyl is independently optionally substituted with halo, hydroxy, amino, oxo, or $OR^{14}$;

wherein $R^{14}$ is H, $C_1$-$C_6$ alkyl, $C_1$-$C_6$ alkenyl, or $C_1$-$C_6$ alkynyl, wherein each hydrogen atom in $C_1$-$C_6$ alkyl, $C_1$-$C_6$ alkenyl, and $C_1$-$C_6$ alkynyl is independently optionally substituted with a halo, hydroxy, or an amino, or a salt thereof.

Embodiment 69 provides the formulation of Embodiment 65, wherein the base oil is a vegetable oil.

While the disclosure has been illustrated and described in detail in the foregoing drawings and description, the same is to be considered as exemplary and not restrictive in character, it being understood that only illustrative embodiments thereof have been shown and described and that all changes and modifications that come within the spirit of the disclosure are desired to be protected.

What is claimed is:

1. A formulation for a lubricant comprising
a base oil comprising a compound of the formula I

wherein $R^1$ is H, $C_1$-$C_6$ alkyl, $C_1$-$C_6$ alkenyl, or $C_1$-$C_6$ alkynyl, wherein each hydrogen atom in $C_1$-$C_6$ alkyl, $C_1$-$C_6$ alkenyl, or $C_1$-$C_6$ alkynyl is independently optionally substituted with halo, hydroxy, amino, oxo, or $OR^3$;

$R^2$ is $C_{10}$-$C_{25}$ alkyl, $C_{10}$-$C_{25}$ alkenyl, or $C_{10}$-$C_{25}$ alkynyl, and wherein each hydrogen atom in $C_{10}$-$C_{25}$ alkyl, $C_{10}$-$C_{25}$ alkenyl, or $C_{10}$-$C_{25}$ alkynyl is independently optionally substituted with halo, hydroxy, amino, oxo, or $OR^7$; or a salt thereof;

a phospholipid; or a salt thereof; and
a salt of the formula

wherein $M^1$ is a divalent cation, $R^9$ and $R^8$ are independently $OC(O)C_{10}$-$C_{25}$ alkyl, $^-OC(O)C_{10}$-$C_{25}$ alkenyl, or $-OC(O)C_{10}$-$C_{25}$ alkynyl, and wherein each hydrogen atom in $C_{10}$-$C_{25}$ alkyl, $C_{10}$-$C_{25}$ alkenyl, or $C_{10}$-$C_{25}$ alkynyl is independently optionally substituted with halo, hydroxy, amino, oxo, or $OR^{10}$, wherein each of $R^3$, $R^7$, and $R^{10}$ is independently H, $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, —C(O)$C_1$-$C_6$ alkyl, —C(O)$C_1$-$C_6$ alkenyl, —C(O)$C_1$-$C_6$ alkynyl, —C(O)$C_{10}$-$C_{25}$ alkyl, —C(O)$C_{10}$-$C_{25}$ alkenyl, —C(O) $C_{10}$-$C_{25}$ alkynyl, wherein each hydrogen atom in $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, —C(O)$C_1$-$C_6$ alkyl, —C(O)$C_1$-$C_6$ alkenyl, —C(O)$C_1$-$C_6$ alkynyl, —C(O) $C_{10}$-$C_{25}$ alkyl, —C(O)$C_{10}$-$C_{25}$ alkenyl, —C(O)$C_{10}$-$C_{25}$ alkynyl is independently optionally substituted with halo, hydroxy, or amino, and further comprising a biocompatible fragrance that is at least 6 wt % of the formulation, the fragrance comprising an essential oil, hexyl acetate fructone ethyl methylphenylglycidate, or combinations thereof, wherein at least the base oil is at least 40% by weight of the formulation.

2. The formulation of claim 1, wherein $R^1$ is H.

3. The formulation of claim 1, wherein $R^1$ is $C_1$-$C_6$ alkyl, and wherein each hydrogen atom in $C_1$-$C_6$ alkyl is independently optionally substituted with halo, hydroxy, amino, oxo, or $OR^3$; or a salt thereof.

4. The formulation of claim 1, wherein $R^1$ is of the formula III

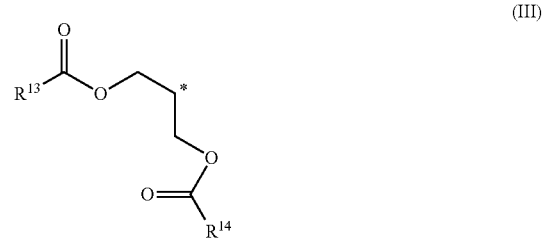

wherein each of $R^{14}$ and $R^{13}$ is independently $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, or $C_{10}$-$C_{25}$ alkynyl, wherein each hydrogen atom in $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, and $C_{10}$-$C_{25}$ alkynyl is independently optionally substituted with halo, hydroxy, or amino; and

* denotes a point of attachment.

5. The formulation of claim 1, wherein $R^7$ is independently H, $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, $C_{10}$-$C_{25}$ alkynyl, and wherein each hydrogen atom in $C_1$-$C_6$ alkyl, $C_1$-$C_6$ alkenyl, $C_1$-$C_6$ alkynyl, $C_{10}$-$C_{25}$ alkyl, $C_{10}$-$C_{25}$ alkenyl, and $C_{10}$-$C_{25}$ alkynyl is independently optionally substituted with halo, hydroxy, or amino; or a salt thereof.

6. The formulation of claim 1, wherein the base oil has a smoke point of at least 450° F., at least 475° F. at least 490° F. at least 500° F., or at least 510° F.

7. The formulation of claim 1, wherein the fragrance is about 6% to about 25% by weight of the formulation.

8. The formulation of claim 1, wherein compound of formula I is at least 20% by weight of the base oil.

9. The formulation of claim 1, wherein the phospholipid has a structure according to formula II

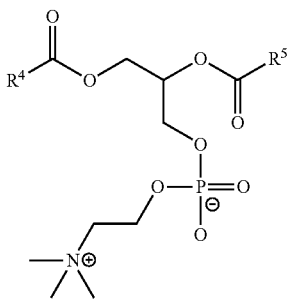

(IV)

wherein each of $R^4$ and $R^5$ is independently $C_{10}$-$C_{25}$ alkyl, $C_{10}$-$C_{25}$ alkenyl, or $C_{10}$-$C_{25}$ alkynyl, and wherein each hydrogen atom in $C_{10}$-$C_{25}$ alkyl, $C_{10}$-$C_{25}$ alkenyl, and $C_{10}$-$C_{25}$ alkynyl is independently optionally substituted with halo, hydroxy, amino, oxo, or $OR^6$;

wherein $R^6$ is H, $C_1$-$C_6$ alkyl, $C_1$-$C_6$ alkenyl, or $C_1$-$C_6$ alkynyl, and wherein each hydrogen atom in $C_1$-$C_6$ alkyl, $C_1$-$C_6$ alkenyl, and $C_1$-$C_6$ alkynyl is independently optionally substituted with halo, hydroxy, or amino, or a salt thereof.

10. The formulation of claim 1, wherein the phospholipid or a salt thereof is at least 2% by weight of the formulation.

11. The formulation of claim 1, wherein the salt of formula II is calcium stearate.

12. The formulation of claim 1, further comprising a compound of formula V

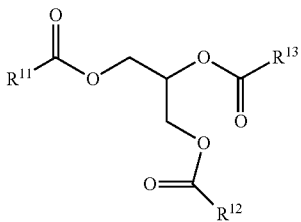

(V)

wherein each of $R^{11}$, $R^{12}$, and $R^{13}$ is independently $C_{10}$-$C_{25}$ alkyl, $C_{10}$-$C_{25}$ alkenyl, or $C_{10}$-$C_{25}$ alkynyl, and wherein each hydrogen atom in $C_{10}$-$C_{25}$ alkyl, $C_{10}$-$C_{25}$ alkenyl, or $C_{10}$-$C_{25}$ alkynyl is independently optionally substituted with halo, hydroxy, amino, oxo, or $OR^{14}$;

wherein $R^{14}$ is H, $C_1$-$C_6$ alkyl, $C_1$-$C_6$ alkenyl, or $C_1$-$C_6$ alkynyl, wherein each hydrogen atom in $C_1$-$C_6$ alkyl, $C_1$-$C_6$ alkenyl, and $C_1$-$C_6$ alkynyl is independently optionally substituted with a halo, hydroxy, or an amino, a long chain alcohol, a saturated fatty acid, a mixture thereof, or salts thereof.

13. A method of coating an electrocautery device with a formulation according to claim 1, the method comprising contacting a surface of an electrocautery device with the formulation according to claim 1.

14. A method of preparing the formulation according claim 12, comprising
heating a base oil,
mixing the base oil with a compound of formula V, and
mixing the base oil with a phospholipid.

15. The method of claim 14, wherein the step of heating comprising heating the base oil to a temperature of about 120° F. to about 225° F.

16. The method of claim 14, wherein the step of mixing the base oil with the compound of formula V occurs before the step of mixing the base oil with the phospholipid.

17. A kit comprising
a formulation for a lubricant according to claim 1, and
a cautery probe.

18. A method of cauterization comprising
applying a formulation for a lubricant according to claim 1 to a cautery probe, and
cauterizing tissue with the cautery probe.

19. The formulation of claim 18, wherein the triglyceride comprises a compound of formula V

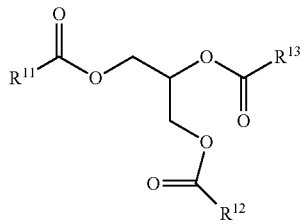

(V)

wherein each of $R^{11}$, $R^{12}$, and $R^{13}$ is independently $C_{10}$-$C_{25}$ alkyl, $C_{10}$-$C_{25}$ alkenyl, or $C_{10}$-$C_{25}$ alkynyl, and wherein each hydrogen atom in $C_{10}$-$C_{25}$ alkyl, $C_{10}$-$C_{25}$ alkenyl, or $C_{10}$-$C_{25}$ alkynyl is independently optionally substituted with halo, hydroxy, amino, oxo, or $OR^{14}$;

wherein $R^{14}$ is H, $C_1$-$C_6$ alkyl, $C_1$-$C_6$ alkenyl, or $C_1$-$C_6$ alkynyl, wherein each hydrogen atom in $C_1$-$C_6$ alkyl, $C_1$-$C_6$ alkenyl, and $C_1$-$C_6$ alkynyl is independently optionally substituted with a halo, hydroxy, or an amino, or a salt thereof.

20. The formulation of claim 19, wherein the base oil is a vegetable oil.

* * * * *